(12) United States Patent
Scutt

(10) Patent No.: US 8,987,476 B2
(45) Date of Patent: *Mar. 24, 2015

(54) SPIRO EPOXIDES AS INTERMEDIATES

(71) Applicant: Syngenta Limited, Guildford, Surrey (GB)

(72) Inventor: James Nicholas Scutt, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/157,685

(22) Filed: Jan. 17, 2014

(65) Prior Publication Data

US 2014/0135508 A1     May 15, 2014

Related U.S. Application Data

(62) Division of application No. 13/375,223, filed as application No. PCT/EP2010/057121 on May 25, 2010, now Pat. No. 8,680,299.

(30) Foreign Application Priority Data

May 29, 2009 (GB) .................................. 0909303.0
Dec. 4, 2009 (GB) .................................. 0921345.5

(51) Int. Cl.
| | | |
|---|---|---|
| *C07D 307/62* | (2006.01) | |
| *C07D 335/02* | (2006.01) | |
| *C07D 303/00* | (2006.01) | |
| *C07D 493/10* | (2006.01) | |
| *C07D 309/32* | (2006.01) | |
| *C07D 309/30* | (2006.01) | |

(52) U.S. Cl.
CPC ............ *C07D 493/10* (2013.01); *C07D 309/32* (2013.01); *C07D 309/30* (2013.01)
USPC .............................. 549/317; 549/28; 549/332

(58) Field of Classification Search
USPC ........................................... 549/28, 332, 317
See application file for complete search history.

(56) References Cited

U.S. PATENT DOCUMENTS 8,680,299 B2 * 3/2014 Scutt ............................ 549/332

FOREIGN PATENT DOCUMENTS

| WO | 2008/071405 | 6/2008 |
| WO | 2009/074314 | 6/2009 |

OTHER PUBLICATIONS

Dorwald F. A. Side Reactions in Organic Synthesis, 2005, Wiley: VCH, Weinheim p. IX of Preface p. 1-15.*
Poschenrieder et al: "Azagrevellins, Part I. Grevellin Analogs with Affinity to the N-Methyl-D-aspartate (Glycine Site) Receptor, a Novel Lead Structure" Arch. Pharm. Pharm. Med. Chem., vol. 333, 2000, pp. 211-216.
Stachel et al.: "Synthese von I, 2-Thiasinen und 1,2-Thiazepinen durch Ringerweiterung", Arch. Pharm., vol. 325, 1992, pp. 461-464.

* cited by examiner

*Primary Examiner* — Nizal Chandrakumar
(74) *Attorney, Agent, or Firm* — James Cueva

(57) ABSTRACT

The present disclosure relates to compounds of formula I

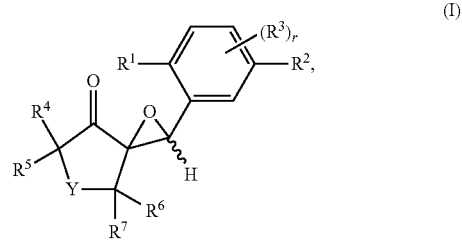

wherein the substituents are as defined in claim 1. The compounds are suitable intermediates in the preparation of herbicidally active 4-phenyl-3,5-pyrandiones, 4-phenyl-3,5-thiopyrandiones and 6-phenylcyclohexane-1,3,5-triones.

20 Claims, No Drawings

SPIRO EPOXIDES AS INTERMEDIATES

This application is a divisional of U.S. patent application Ser. No. 13/375,223, filed Nov. 29, 2011, which was a 371 of International Application No. PCT/EP2010/057121 filed May 25, 2010, which claims priority to GB 0909303.0 filed May 29, 2009, and GB 0921345.5 filed Dec. 4, 2009, the contents of which are incorporated herein by reference.

The present invention relates to novel compounds, their preparation and their use as intermediates in the preparation of herbicidally active substituted 4-phenyl-3,5-pyrandiones, 4-phenyl-3,5-thiopyrandiones and 6-phenylcyclohexane-1,3,5-triones.

4-Phenyl-3,5-pyrandiones, 4-phenyl-3,5-thiopyrandiones and 6-phenylcyclohexane-1,3,5-triones having herbicidal action and a process for the preparation of these compounds are described, for example, in WO 08/071,405.

It has now been discovered that certain substituted epoxyketones can be used as key intermediates in the process for preparing such herbicidally active diones and triones. These are now obtainable in high yield and with considerable advantages over the known processes.

The present invention accordingly relates to compounds of formula I

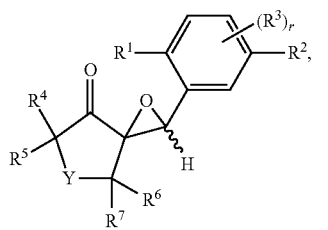

wherein
$R^1$ is halogen, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl;
$R^2$ is hydrogen, halogen, methylsulfonyloxy, $C_1$-$C_4$haloalkylsulfonyloxy, p-tolylsulfonyloxy, optionally substituted aryl or optionally substituted heteroaryl;
r is 0, 1, 2 or 3;
$R^3$, if r is 1, is $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, cyano or nitro; or the substituents $R^3$, if r is 2 or 3, independently of each other, are $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, cyano or nitro;
Y is O, S, SO, $SO_2$ or CO;
$R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, cyclopropyl or cyclopropyl substituted by $C_1$- or $C_2$alkyl, $C_1$- or $C_2$haloalkyl or halogen; cyclobutyl or cyclobutyl substituted by $C_1$- or $C_2$alkyl; oxetanyl or oxetanyl substituted by $C_1$- or $C_2$alkyl; $C_5$-$C_7$cycloalkyl or $C_5$-$C_7$cycloalkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl or $C_4$-$C_7$cycloalkenyl substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; cyclopropyl$C_1$-$C_5$alkyl or cyclopropyl$C_1$-$C_5$alkyl substituted by $C_1$- or $C_2$alkyl, $C_1$- or $C_2$haloalkyl or halogen; cyclobutyl$C_1$-$C_5$alkyl or cyclobutyl$C_1$-$C_5$alkyl substituted by $C_1$- or $C_2$alkyl; oxetanyl$C_1$-$C_5$alkyl or oxetanyl$C_1$-$C_5$alkyl substituted by $C_1$- or $C_2$alkyl; $C_5$-$C_7$ cycloalkyl$C_1$-$C_5$alkyl or $C_5$-$C_7$cycloalkyl$C_1$-$C_5$alkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl$C_1$-$C_5$ alkyl or $C_4$-$C_7$cycloalkenyl$C_1$-$C_5$alkyl which is substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; benzyl or benzyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl;
or
$R^4$ and $R^5$, or $R^6$ and $R^7$, are joined to form a 5-7 membered saturated or unsaturated ring in which a methylene group is optionally replaced by an oxygen or sulfur atom, or a 5-7 membered saturated or unsaturated ring substituted by $C_1$- or $C_2$alkyl, where a methylene group of the ring is optionally replaced by an oxygen or sulfur atom; or
$R^4$ and $R^7$ are joined to form a 5-7 membered saturated or unsaturated ring unsubstituted or substituted by $C_1$- or $C_2$alkyl, $C_1$- or $C_2$alkoxy, $C_1$- or $C_2$alkoxy$C_1$- or $C_2$alkyl, hydroxy, halogen, phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl.

The present invention also relates to a new process for the preparation of the compounds of formula I.

The invention further relates to a process for the preparation of 4-phenyl-3,5-pyrandiones, 4-phenyl-3,5-thiopyrandiones and 6-phenylcyclohexane-1,3,5-triones of formula (A) which is shown below, using the compounds of the formula I as intermediates.

In the substituent definitions of the compounds of the formula I, the alkyl substituents and (halo)alkyl moieties of alkoxy, alkylthio etc. having 1 to 6 carbon atoms are preferably methyl, ethyl, propyl, butyl, pentyl and hexyl, in the form of their straight and branched isomers. Suitable cycloalkyl groups contain 3 to 7 carbon atoms and are for example cyclopropyl, cyclobutyl, cyclopentyl, cyclohexyl and cycloheptyl. Cyclopropyl, cyclobutyl, cyclopentyl and cyclohexyl are preferred. Suitable cycloalkene groups contain 4 to 7 carbon atoms and may contain up to 3 double bonds. Preferred halogens are fluorine, chlorine and bromine. Preferred examples of aryls are phenyl and naphthyl. Preferred examples of heteroaryls are thienyl, furyl, pyrrolyl, isoxazolyl, oxazolyl, oxetanyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl and pyridazinyl, and, where appropriate, N-oxides and salts thereof. These aryls and heteroaryls can be substituted by one or more substituents, where preferred substituents are halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

In a preferred group of compounds of formula I, $R^1$ is halogen, $C_1$-$C_4$alkyl, $C_1$-$C_4$haloalkyl, $C_3$-$C_6$cycloalkyl or $C_1$-$C_4$-haloalkoxy.

In another preferred group of compounds of formula I, $R^2$ is halogen, aryl or heteroaryl; or aryl or heteroaryl both substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, phenoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_3$-$C_6$cycloalkyl, $C_1$-$C_4$alkylsulfonyloxy, $C_1$-$C_4$haloalkylsulfonyloxy, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, nitro, cyano, thiocyanato, hydroxy, amino, $C_1$-$C_6$alkylamino, $C_1$-$C_6$dialkylamino, $C_3$-$C_6$cycloalkylamino, morpholino, thiomorpholino, $C_1$-$C_6$alkylcarbonylamino, $C_1$-$C_6$alkoxycarbonylamino, $C_3$-$C_6$ alkenyloxycarbonylamino, $C_3$-$C_6$ alkynyloxycarbonylamino, $C_1$-$C_6$ alkylaminocarbonylamino, di($C_6$alkyl)aminocarbonylamino, formyl, $C_1$-$C_6$alkyl-carbonyl, $C_2$-$C_6$alkenylcarbonyl, $C_2$-$C_6$alkynylcarbonyl, carboxy, $C_1$-$C_6$alkoxycarbonyl, $C_3$-$C_6$alkenyloxycarbonyl, $C_3$-$C_6$alkynyloxycarbonyl, carboxamido, $C_1$-$C_6$alkylaminocarbonyl, di($C_1$-$C_6$alkyl)aminocarbonyl, $C_1$-$C_6$alkylcarbonyloxy, $C_1$-$C_6$alkylaminocarbonyloxy, di($C_1$-$C_6$alkyl)aminocarbonyloxy or $C_1$-$C_6$alkylthiocarbonylamino.

Preferably, $R^2$ in the compounds of formula I is halogen, aryl or heteroaryl; or aryl or heteroaryl both substituted by halogen, $C_1$-$C_4$alkyl, $C_1$-$C_4$haloalkyl, phenoxy, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

More preferably, $R^2$ is phenyl, thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, pyridazinyl, oxadiazolyl and thiadiazolyl, and N-oxides and salts thereof, where these rings are unsubstituted or substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

In even more preferred compounds of the formula I, $R^2$ is phenyl or pyridyl or phenyl or pyridyl both substituted by halogen, nitro, cyano, $C_1$-$C_2$alkyl, $C_1$-$C_2$haloalkyl, $C_1$-$C_2$alkoxy or $C_1$-$C_2$haloalkoxy.

In an especially preferred group of compounds, $R^2$ is phenyl substituted at the para-position by halogen (in particular chlorine) and is optionally further substituted by halogen, nitro, $C_1$-$C_2$alkyl, $C_1$-$C_2$haloalkyl, $C_1$-$C_2$alkoxy or $C_1$-$C_2$haloalkoxy.

Preferably, $R^3$ is hydrogen (r is 0) or $C_1$-$C_6$alkyl, especially hydrogen.

Preferably, $R^3$, if r is 1, is $C_1$-$C_3$alkyl.

Preferred are those compounds of the formula I, wherein $R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$ alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl; $C_5$-$C_7$cycloalkyl or $C_5$-$C_7$cycloalkyl substituted by $C_1$- or $C_2$alkyl or $C_1$- or $C_2$haloalkyl and in which a methylene group is optionally replaced by an oxygen or sulfur atom or a sulfinyl or sulfonyl group; $C_5$-$C_7$cycloalkyl$C_1$-$C_5$alkyl or $C_5$-$C_7$cycloalkyl$C_1$-$C_5$alkyl substituted by $C_1$-$C_2$alkyl or $C_1$- or $C_2$haloalkyl and in which a methylene group is optionally replaced by an oxygen or sulfur atom or a sulfinyl or sulfonyl group.

More preferably, $R^4$, $R^5$, $R^6$ and $R^7$, independently of each other, are hydrogen, $C_1$-$C_2$alkyl, $C_1$-$C_2$haloalkyl or $C_1$-$C_2$alkoxy$C_1$-$C_2$alkyl.

In a preferred group of compounds of the formula (I), $R^1$ is ethyl, methyl or cyclopropyl, $R^2$ is phenyl or phenyl substituted by halogen or $C_1$-$C_2$alkyl, $R^3$ is hydrogen, $R^4$, $R^5$, $R^6$ and $R^7$, independently of each other, are $C_1$-$C_2$alkyl.

In another preferred group of compounds of the formula (I), $R_1$ is methyl, ethyl, cyclopropyl, n-propyl, halogen, trifluoromethoxy, difluoromethoxy and trifluoromethyl, $R_4$, $R_5$, $R_6$ and $R_7$, independently of each other, are hydrogen, methyl and ethyl, $R_2$ is halogen, phenyl substituted by halogen, $C_1$-$C_4$alkyl, $C_1$-$C_4$haloalkyl, $C_1$-$C_4$haloalkoxy or $C_1$-$C_4$alkoxy, $R_3$ is hydrogen and Y is oxygen, where more preferably, $R_1$ is ethyl or cyclopropyl, $R_4$, $R_5$, $R_6$ and $R_7$ are methyl, $R_2$ is phenyl substituted once or twice by fluorine, chlorine, methoxy or methyl, $R_3$ is hydrogen and Y is oxygen, where most preferably, $R_1$ is ethyl, $R_4$, $R_5$, $R_6$ and $R_7$ are methyl, $R_2$ is 4-chlorophenyl, 2,4-dichlorophenyl and 2-fluoro-4-chlorophenyl, $R_3$ is hydrogen and Y is oxygen.

In another preferred group of compounds of the formula (I), $R_1$ is ethyl, trifluoromethyl, cyclopropyl, difluoromethoxy, trifluoromethoxy, fluoro, bromine or iodine, $R_4$, $R_5$, $R_6$ and $R_7$, independently of each other, are hydrogen or methyl, $R_2$ is bromine, 4-chlorophenyl, 2-fluoro-4-chlorophenyl, 2,4-di-chlorophenyl, $R_3$ is hydrogen and Y is O, where more preferably, $R_1$ is ethyl, cyclopropyl, $R_4$, $R_5$, $R_6$ and $R_7$ are methyl, $R_2$ is bromine, 4-chlorophenyl, 2-fluoro-4-chlorophenyl or 2,4-di-chlorophenyl, $R_3$ is H and Y is O.

In a further aspect of the invention, it has now been found, surprisingly, that the compounds of formula I can easily be converted into 4-phenyl-3,5-pyrandiones, 4-phenyl-3,5-thiopyrandiones and 6-phenylcyclohexane-1,3,5-triones of formula (A) below in the presence of an acid.

Reaction Scheme 1

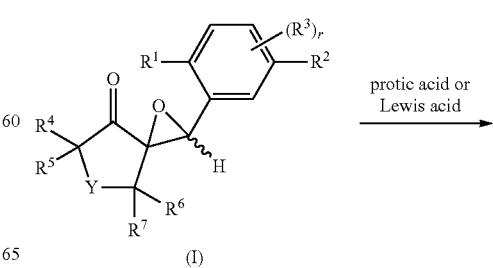

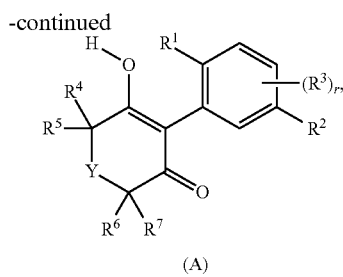

(A)

wherein Y, $R^1$, $R^2$, $R^3$, r, $R^4$, $R^5$, $R^6$ and $R^7$ are as defined above.

Suitable acids include Brönsted acids such as mineral acids and organic acids, for example sulfuric acid, hydrochloric acid, hydrogen chloride, p-toluenesulfonic acid, acetic acid and formic acid, and Lewis acids such as metal halides, for example boron trifluoride, aluminium chloride, iron chloride, tin(IV) chloride, zinc chloride, zinc bromide, lithium perchlorate, as well as metal triflates such as scandium triflate and ytterbium triflate. Mixtures of such acids can also be used. The conversion of a compound of formula (I) into a compound of formula (A) may be considered to be an example of a semi-Pinacol rearrangement (see for example M. Paulson, M. Daliya and C. Asokan, Synth. Commun. (2007), 37(5), 661-665; S. Sankararaman and J. Nesakumar, J. Chem. Soc, Perkin Trans. 1, (1999), (21), 3173-3175; K. Rehse and R. Bienfait, Archiv der Pharmazie, (1984), 317(5), 385-93; H. Kamath, A. Sahasrabudhe, B. Bapat and S. Kulkarni, Indian J. Chem., Section B: (1981), 20B(12), 1094-6; G. Buchanan and D. Jhaveri, J. Org. Chem. (1961), 26 4295-9; and H. House, Richard L. Wasson, J. Am. Chem. Soc., (1956), 78, 4394-400), but such a transformation is unknown for compounds of type (I). The reactions conditions which are useful in the process of the present invention are similar to those described in the literature mentioned above or can be derived by those skilled in the art. Suitable solvents are those chosen to be compatible with the acid used, and include chlorinated hydrocarbons, alcohols, ethers, aromatics and organic acids, for example dichloromethane, dichloroethane, diethyl ether, acetic acid, formic acid, toluene, benzene, methanol, ethanol, isopropanol and tetrahydrofuran. Mixtures of solvents can also be used. Preferably the reaction is performed using concentrated sulphuric acid in dichloroethane. The preferred reaction temperature is within the range of between −50° C. and 83° C., even more preferably between −50° C. and 40° C. Additional preferred reaction conditions are the use of lithium perchlorate solution in ether in combination with 0.1-100 mol % ytterbium triflate as acid, at a temperature range between 0° C. and 60° C.

The present process is distinguished over the art mentioned above by:
(a) easy accessibility of the starting materials,
(b) a short reaction sequence,
(c) avoidance of highly toxic reagents
(d) high volume concentration of the reactants (demonstrated up to 20%, example P1 step 4).
(e) widely—especially in the 2 and 5 positions—substituted phenyl derivatives as starting compounds,
(f) generally high product yields, and
(g) economic and ecological advantages derived from the fact that the process can be used as a partial step in a continuous reaction procedure for the preparation of 4-phenyl-3,5-pyrandiones, 4-phenyl-3,5-thiopyrandiones and 6-phenylcyclohexane-1,3,5-triones of formula (A), which are known to exhibit herbicidal properties.

The present preparation process is therefore suitable especially for the cost-effective, large-scale preparation of the diones and triones of formula (A).

The compounds of formula (I), and this is another aspect of the present invention, can be obtained by the epoxidation of compounds of formula (B), as is illustrated in the following reaction scheme:

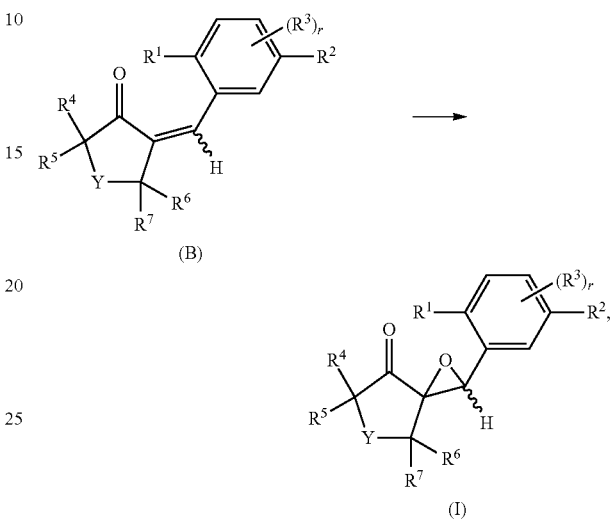

wherein Y, $R^1$, $R^2$, $R^3$, r, $R^4$, $R^5$, $R^6$ and $R^7$ are as defined above. The compounds of the formula (B) are novel and have been especially designed as intermediates for the synthesis of the compounds of formula (I) and form another aspect of the invention.

Epoxidation may be effected by treatment of a compound of formula (B) with a suitable oxidising agent such as an organic peroxide or metal hyperchlorite, for example dimethyldioxirane, sodium hypochlorite, hydrogen peroxide, tert-butyl peroxide or trifluoroperacetic acid, optionally in combination with a suitable base (such as an alkali metal hydroxide or carbonate, alkaline earth metal hydroxide or carbonate, or an amine base such as 1,8-diazabicyclo[5.4.0]-undec-7-ene), optionally in a suitable solvent (such as an alcohol, a halogenated hydrocarbon or an aromatic compound, for example methanol, ethanol, dichloromethane or toluene) and at a suitable temperature. The reaction can also be performed under biphasic conditions, in which a phase-transfer reagent is also typically used in 0.001-50 mol %. The phase transfer reagent is preferably a quaternary ammonium salt, a crown ether, a polyethylene glycol, or phosphonium salt. and at a suitable temperature. Similar reactions are known in the literature (see for example, I. K. Korobitsyna, O. P. Studzinskii, The Russian Journal of Organic Chemistry (1969), 5(8), 1493-5; A. Halasz, Z. Jambor, A. Levai, C. Nemes, T. Patonay and G. Toth, J. Chem. Soc, Perkin Trans. 1, (1996), (4), 395-400; N. Yousif, F. Gad, A. Fahmy, M. Amine and H. Sayed, Phosphorus, Sulfur and Silicon and the Related Elements (1996), 117, 11-19; T. Ooi, D. Ohara, M. Tamura and K. Maruoka, J. Am. Chem. Soc., (2004), 126(22), 6844-6845; A. Amr, H. Hayam and M. Abdulla, Archiv der Pharmazie, (2005), 338(9), 433-440; K. Drauz, S. M. Roberts, T. Geller and A. Dhanda, U.S. Pat. No. 6,538,105 B1; and L. S. Chagonda and B. A. Marples, J. Chem. Soc. Perkin 1, 1988, 875-879). Mixtures of oxidising agents, bases, and solvents can also be used. Preferably, epoxidation is carried out using hydrogen peroxide and a metal hydroxide (especially lithium hydroxide or sodium hydroxide), in methanol at a temperature of between −10° C. and 60° C.

A compound of formula (B) may be prepared from a compound of formula (C) by condensation with a benzaldehyde of formula (D), in the presence of a suitable base and optionally in the presence of a suitable solvent (see for example, A. Lagrange, S. Forestier, G. Lang and B. Luppi, EP368717 A1; D. C. Rowlands, U.S. Pat. No. 2,776,239; and E. Tamate, Journal of the Chemical Society of Japan, (1957), 78, 1293-7).

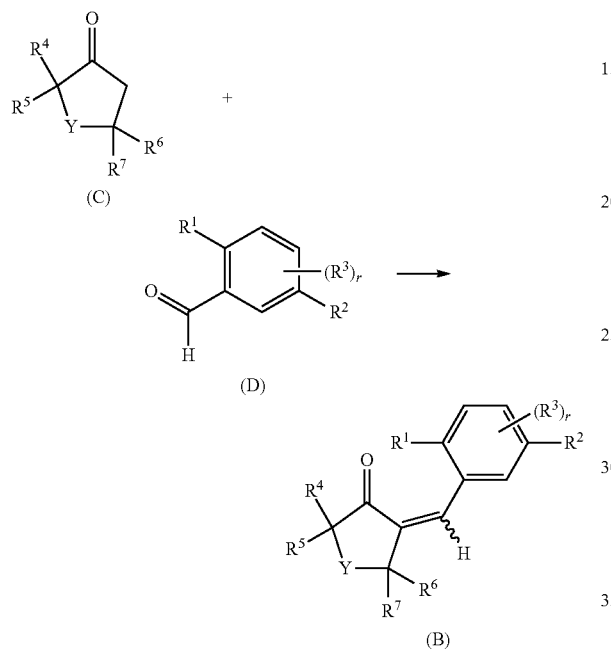

Preferably the base is a metal hydroxide, such as sodium hydroxide or potassium hydroxide, or a metal alkoxide such as sodium methoxide, sodium ethoxide or potassium tert-butoxide. Preferably the solvent is dimethoxyethane, dioxane, tetrahydrofuran, diethyl ether or an alkyl alcohol, such as methanol, ethanol or isopropanol. Mixtures of bases and, in particular, solvents can also be used.

Compounds of formula (C), wherein Y is O, are known compounds (see for example M. Newman and W. Reichle, Org. Synth. Coll. Vol. V., (1973), 1024; Y. Zal'kind, E. Venus-Danilova and V. Ryabtseva, Russian Journal of General Chemistry, (1950), 20, 2222-9; M. Bertrand, J. Dulcere, G. Gil, J. Grimaldi and P. Sylvestre-Panthet, Tetrahedron Letters (1976), (18), 1507-8), or may be prepared from known compounds by known methods. Compounds of formula (C), wherein Y is C=O, are known compounds (see for example N. J. Turro, D. R. Morton, E. Hedaya, M. E. Kent, P. D'Angelo, P. Schissel, Tetrahedron Letters (1971), (27), 2535-8; P. A. Krapcho, D. R. Rao, M. P. Silvon, B. Abegaz, Journal of Organic Chemistry (1971), 36(25), 3885-90; S, N. Crane, T. J. Jenkins, D. J. Burnell, Journal of Organic Chemistry (1997), 62(25), 8722-8729; S, N. Crane, D. J. Burnell, Journal of Organic Chemistry (1998), 63(4), 1352-1355; S, N. Crane, D. J. Burnell, Journal of Organic Chemistry (1998), 63(16), 5708-5710; C. E. Elliott, D. O. Miller, D. J. Burnell, Journal of the Chemical Society, Perkin Transactions 1 (2002), (2), 217-226), or may be prepared from known compounds by known methods. Compounds of formula (C), wherein Y is S, SO or $SO_2$ are known compounds (see for example E. R. Buchman, H. Cohen, Journal of the American Chemical Society (1944), 66, 847-8; A. W. D. Avison, F. Bergel, J. W. Haworth, U.S. Pat. No. 2,408,519: K. G. Mason, M. A. Smith, E. S. Stern, E J. A. Elvidge, Journal of the Chemical Society [Section] C: Organic (1967), (21), 2171-6; T. A. Magee, Thomas A. DE 2033454; I. Tabushi, Y. Tamaru, Z. Yoshida, T. Sugimoto, Journal of the American Chemical Society (1975), 97(10), 2886-91; P. E. Aldrich, G. H. Berezin, B. I. Dittmar, I. Bruce, DE 2516554; I. Tabushi, Y. Tamaru, Z. Yoshida, Bulletin of the Chemical Society of Japan (1978), 51(4), 1178-82; D. N. Reinhoudt, J. Geevers, W. P. Trompenaars, S. Harkema, G. J. Van Hummel, Journal of Organic Chemistry (1981), 46(2), 424-34; F. Duus, Synthesis (1985), (6-7), 672-4; J. Schatz, Science of Synthesis (2002), 9, 287-422), or may be prepared from known compounds by known methods.

Compounds of formula (D) are either known compounds, or can be prepared by formylation of a compound of formula (E) wherein Hal is chlorine, bromine or iodine (preferably bromine or iodine).

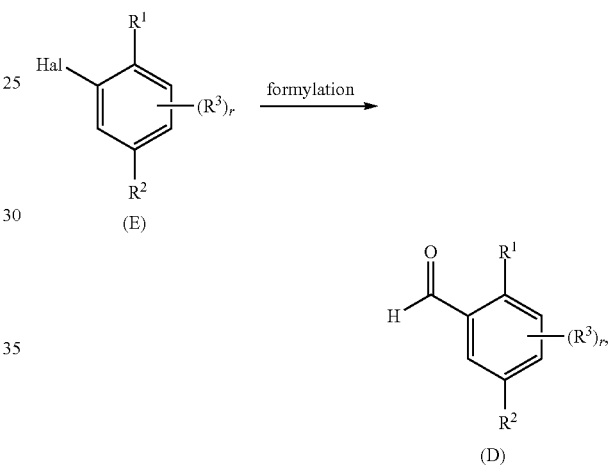

wherein $R^1$, $R^2$, $R^3$ and r and Hal is halogen as defined above. Preferred compounds of the formula (D) are the compounds of the formula (D1)

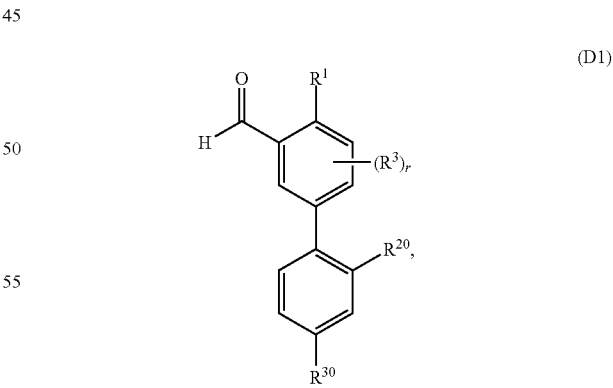

wherein $R^1$, $R^3$ and r as defined above and $R^{20}$ and $R^{30}$, independently of each other, are hydrogen, methyl, methoxy, fluorine, chlorine or bromine. The compounds of the formula (D) as far as they are novel and the novel compounds of the formula (D1) have been especially designed as intermediates for the synthesis of the compounds of formula (I) and form another aspect of the invention.

Suitable conditions for effecting the formylation of aryl halides are known, and include, for example, the treatment of an aryl halide with a suitable organometallic reagent (such as isopropyl magnesium chloride, n-butyllithium, sec-butyllithium or tert-butyllithium), or by treatment with a suitable alkali metal or alkali earth metal (such as lithium or magnesium) in a suitable solvent (such as diethyl ether, dimethoxyethane or tetrahydrofuran). The resulting arylmetal reagent is then reacted with a suitable formylating agent such as N,N-dimethylformamide or N-formylmorpholine. Alternatively a compound of formula (D) may be prepared from a compound of formula (E) (wherein Hal can also be a pseudohalogen such as triflate) by treatment with a carbonylating agent (such as carbon monoxide) in the presence of a suitable catalyst, base, and reducing agent (see for example L. Ashfield and C. Barnard, Org. Process Res. Dev., 11 (1), 39-43, 2007). Compounds of formula (E) are either known compounds (see for example WO 2008/071405), or may be synthesised from known intermediates using standard chemical transformations.

Alternatively a compound of formula (I) may be prepared by reacting a compound of formula (F) (wherein halogen is chlorine, bromine or iodine, preferably chlorine or bromine) with a compound of formula (D), as illustrated in the following reaction scheme.

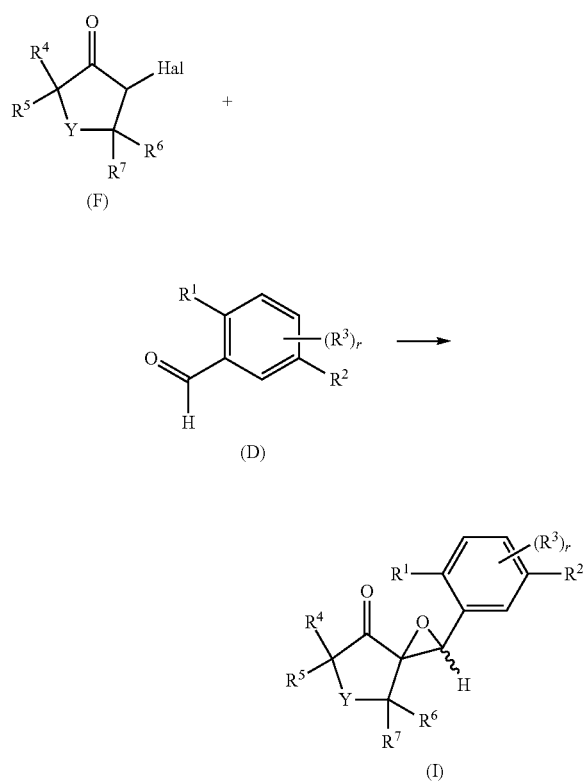

The reaction of (F) and (D) can be performed with a suitable base, optionally in a suitable solvent, at a suitable temperature. Preferably the base is an alkali or alkali earth metal hydroxide (such as sodium hydroxide, lithium hydroxide or potassium hydroxide), an alkali or alkali earth metal alkoxide (such as sodium methoxide, sodium ethoxide or potassium tert-butoxide), an alkali or alkali earth metal carbonate (such as potassium carbonate or sodium carbonate, or sodium bicarbonate), a metal amide (such as lithium diisopropylamide, lithium hexamethyldisilazide or lithium 2,2,6,6-tetramethylpiperidide), an organometallic (such as butyl lithium or ethylmagnesium bromide) or a metal hydride (such as sodium hydride or potassium hydride). Suitable solvents include chlorinated hydrocarbons, ethers, alcohols, aromatics and various polar aprotic solvents, for example 1,2-dimethoxyethane, tetrahydrofuran, 1,4-dioxane, diethyl ether, dibutyl ether, dichloromethane, dichloroethane, acetonitrile, dimethyl sulfoxide, benzene, toluene, methanol, ethanol, isopropanol or tert-butanol, and is chosen to be compatible with the base under the reaction conditions. The reaction can also be performed under biphasic conditions, in which a phase-transfer reagent is also typically used in 0.001-50 mol %. The phase transfer reagent is preferably a quaternary ammonium salt, a crown ether, a polyethylene glycol, or phosphonium salt. Most preferably the reaction is performed using lithium diisopropylamide in tetrahydrofuran at a temperature range of −100° C. to 60° C. The conversion of a compound of formula (F) into a compound of formula (I) may be considered to be an example of a Darzens condensation (see for example, W. N. Wassef, M. M. El-Barky, Journal of Chemical Research, Synopses (1990), (12), 402-3; J. Li, X. Liu, X. Li, Youji Huaxue (2007), 27(11), 1428-1431; Y. Tong, Y. Cheng, X. Guo, S. Wu, Hecheng Huaxue (2007), 15(1), 102-104; C. Parmenon, J. Guillard, D. Caignard, N. Hennuyer, B. Steels, V. Audinot-Bouchez, J. Boutin, C. Dacquet, A. Ktorza, M. Viaud-Massuard, Bioorganic & Medicinal Chemistry Letters (2008), 18(5), 1617-1622; H. Xiao, X. Han, J. Xiong, Faming Zhuanli Shenqing Gongkai Shuomingshu (2007), p 11; J. M. Concellon, E. Bardales, R. Llavona, Journal of Organic Chemistry (2003), 68(4), 1585-1588), but such a transformation is unknown for compounds of type (F).

Compounds of formula (F), wherein Y is O, are either known compounds (see for example H. Richet, R. Dulou, R., G. Dupont, Bulletin de la Societe Chimique de France (1947), 693-9; H. Richet, Ann. Chim. [12] (1948), 3 317-54; I. K. Korobitsyna, Yu. K. Yur'ev, Yu. A. Cheburkov, E. M. Lukina, Russian Journal of General Chemistry (1955), 25, 734-8; I. K. Korobitsyna, Yu. K. Yur'ev, Yu. A. Cheburkov, E. M. Lukina, Russian Journal of General Chemistry (1955), 25, 690-702; F. Leonard, A. Wajngurt, H. Horn, Journal of Organic Chemistry (1956), 21, 1400-4; I. K. Korobitsyna, I. G. Zhukova, V. A. Kuvshinova, N. N. Gaidamovich, Yu. K. Yur'ev, Doklady Akademii Nauk SSSR (1957), 114, 327-30; I. K. Korobitsyna, I. G. Zhukova, I. G, Yu. K. Yur'ev, Russian Journal of General Chemistry (1959), 29, 2190-6; I. K. Korobitsyna, L. L. Rodina, L. M. Stashkova, Chemistry of Heterocyclic Compounds (1966), (6), 843-7; G. Hoehne, F. Marschner, K. Praefcke, P. Weyerstahl, Chem. Ber. (1975), 108(2), 673-82; H. Saimoto, T. Hiyama, H. Nozaki, Bull. Chem. Soc. Jpn., (1983), 56(10), 3078-87; A. M. Zvonok, N. M. Kuz'menok, I. G. Tishchenko, L. S. Stanishevskii, Russian Journal of General Chemistry (1985), 21(6), 1330-4) or can be prepared from compounds of formula (C) under known conditions. Compounds of formula (F), wherein Y is S, SO and $SO_2$, are either known compounds (see for example M. Polievka, L. Uhlar, V. Patek, Petrochemia (1973), 13(5-6), 156-60; N. N. Novitskaya, B. V. Flekhter, G. M. Prokhorov, A. S. Lukmanova, G. A. Tolstikov, G. V. Leplyanin, S. A. Lange, M. V. Strashnov, SU 468920 A1; P. H. McCabe, W. Routledge, Tetrahedron Letters (1976), (1), 85-6; T. S. Chou, C. Y. Tsai, Tetrahedron Letters (1992), 33(29), 4201-4), or can be prepared from compounds of formula (C) under known conditions. Compounds of formula (F), wherein Y is C=O, can be prepared from compounds of formula (C) under similar halogenation conditions. The Examples that follow further illustrate the invention without limiting it.

PREPARATION EXAMPLES

Example P1

Preparation of 4-(5-bromo-2-ethylphenyl)-2,2,6,6-tetramethylpyran-3,5-dione

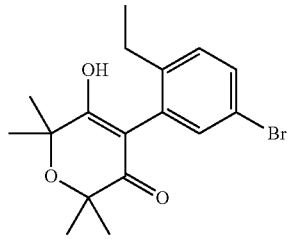 [SMILES: CCc1ccc(Br)cc1C1=C(O)C(C)(C)OC(C)(C)C1=O]

Step 1: Preparation of 5-Bromo-2-ethyl-benzaldehyde

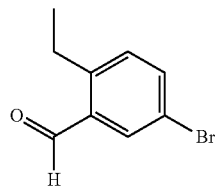

To a solution of 4-bromo-1-ethyl-2-iodobenzene (31.8 g, 103 mmol) (described in WO 2008/071405) in anhydrous tetrahydrofuran (250 ml) at −20° C. is added isopropyl magnesium chloride (55 ml, 110 mmol, 2M solution in tetrahydrofuran) dropwise over 10 minutes. Once the addition is complete the reaction mixture is stirred at −20° C. for 3 hours, followed by dropwise addition of anhydrous N,N-dimethylformamide (16.0 ml, 200 mmol). The reaction mixture is stirred at room temperature for a further 2.5 hours, then left to stand overnight. 2M hydrochloric acid (90 ml) is added and the crude product is extracted into dichloromethane. Organics are combined, dried over magnesium sulfate then filtered and the filtrate evaporated under reduced pressure to afford 5-bromo-2-ethyl-benzaldehyde (21.20 g) as an orange liquid.

Step 2: Preparation of 4-(5-Bromo-2-ethylbenzylidene)-2,2,5,5-tetramethyldihydrofuran-3-one

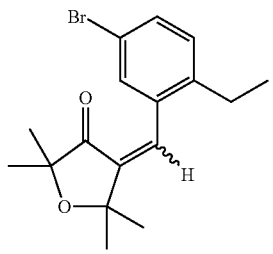 [SMILES: CCc1ccc(Br)cc1C=C1C(=O)C(C)(C)OC1(C)C]

To an ice-cold solution of dihydro-2,2,5,5-tetramethyl-3 (2H)-furanone (13.4 g, 94.34 mmol) in anhydrous 1,2-dimethoxyethane (32 ml) is added sodium methoxide (5.6 g, 103.8 mmol) in one portion, and the reaction mixture is stirred at this temperature for 5 minutes. To the resulting slurry is then added a solution of 5-bromo-2-ethyl-benzaldehyde (20 g, 94.34 mmol) in 1,2-dimethoxyethane (32 ml) dropwise over 10 minutes. The solution is next stirred at 0° C. for 1 hour, then diluted with diethyl ether and washed with 2M hydrochloric acid (×2). Organic fractions are combined, dried over magnesium sulphate, filtered and the filtrate evaporated in vacuo to afford 4-(5-bromo-2-ethylbenzylidene)-2,2,5,5-tetramethyldihydrofuran-3-one (30.2 g) as a yellow liquid.

Step 3: Preparation of 2-(5-Bromo-2-ethylphenyl)-4,4,6,6-tetramethyl-1,5-dioxaspiro[2.4]heptan-7-one

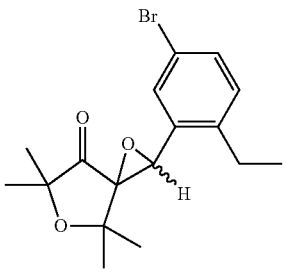 [SMILES: CCc1ccc(Br)cc1C1OC12C(=O)C(C)(C)OC2(C)C]

To a solution of 4-(5-bromo-2-ethylbenzylidene)-2,2,5,5-tetramethyldihydrofuran-3-one (32.07 g, 95.15 mmol) in methanol (1570 ml) at 35° C. is added 50% aqueous hydrogen peroxide (8.10 ml, 142.73 mmol), followed immediately by a solution of 2M aqueous lithium hydroxide (9.51 ml, 19.03 mmol). This reaction mixture is stirred at 35° C. for exactly 1 hour, then quenched with saturated sodium metabisulfite (340 ml) and distilled water (340 ml). After stirring at room temperature for 15 minutes solvents are then concentrated in vacuo (to approximately 500 ml), over which time the product precipitates as a yellow solid. To this suspension is added distilled water (500 ml), and the product is isolated by filtration. After additional washing with distilled water the solid is dried under vacuum overnight to afford 2-(5-bromo-2-ethylphenyl)-4,4,6,6-tetramethyl-1,5-dioxaspiro[2.4]heptan-7-one (29.30 g) as a yellow solid which is used without purification in the next step.

1H NMR (CDCl$_3$): δ 7.47-7.40 (m, 2H), 7.10 (d, 1H), 4.43 (s, 1H), 2.62-2.60 (m, 2H), 1.40 (s, 3H), 1.37 (s, 3H), 1.30-1.20 (m, 6H), 0.78 (s, 3H).

Step 4: Preparation of 4-(5-bromo-2-ethylphenyl)-2,2,6,6-tetramethylpyran-3,5-dione

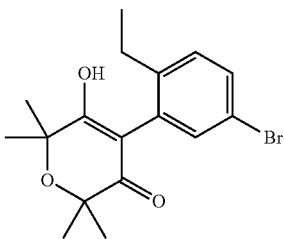 [SMILES: CCc1ccc(Br)cc1C1=C(O)C(C)(C)OC(C)(C)C1=O]

To an ice-cold solution of concentrated sulphuric acid (2 ml) is added a second solution of 2-(5-bromo-2-ethylphenyl)-4,4,6,6-tetramethyl-1,5-dioxaspiro[2.4]heptan-7-one (0.995 g, 2.82 mmol) in 1,2-dichloroethane (2 ml) dropwise over 5 minutes. This biphasic mixture is stirred vigorously for 1 hour at 0° C., then poured into ice-cold water (15 ml). This aqueous mixture is then concentrated under vacuum to remove all organic volatiles, producing a free-flowing solid. The solid is filtered, dried under vacuum, then washed with hexanes to afford 4-(5-bromo-2-ethylphenyl)-2,2,6,6-tetramethylpyran-3,5-dione (0.81 g) as a cream-coloured solid.

1H NMR (CDCl$_3$): δ7.48 (1H, dd), 7.23-7.21 (2H, m), 5.60 (1H, s), 2.45-2.33 (2H, m), 1.60 (6H, d), 1.48 (6H, d), 1.10 (3H, t).

Example P2

Preparation of 4-(5-Bromo-2-ethylphenyl)-2,2,6-trimethylpyran-3,5-dione

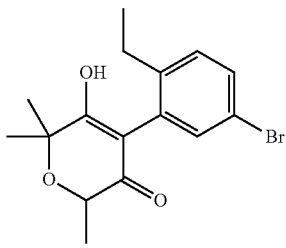 [SMILES: CCc1ccc(Br)cc1C1=C(O)C(C)(C)OC(C)C1=O]

Step 1: Preparation of 4-Bromo-2,2,5-trimethyldihydro-furan-3-one

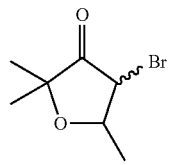

To a solution of acetic acid 4-bromo-2,2,5-trimethyl-2,5-dihydrofuran-3-yl ester (19.14 g, 0.11 mol) (described in T. Hiyama et al. Bull. Chem. Soc. Jpn., 56, 3078-3087 (1983)) in anhydrous chloroform (75 ml) at −20° C. is added a solution of bromine (18.00 g, 0.11 mol) in anhydrous chloroform (200 ml) dropwise over 45 minutes. After stirring at this temperature for 30 minutes the reaction mixture was allowed to warm to room temperature, then further stirred for 1 hour. After dilution with chloroform (250 ml) the organic phase is washed with dilute aqueous sodium bicarbonate then brine, and the phases separated. Organics solvents are removed under reduced pressure to afford 4-bromo-2,2,5-trimethyldihydro-furan-3-one (23.50 g) as a dark orange oil. This material is used without purification in the next step.

Step 2: Preparation of 2-(5-Bromo-2-ethylphenyl)-4,6,6-trimethyl-1,5-dioxaspiro[2.4]heptan-7-one

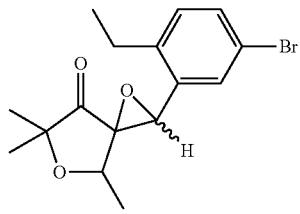 [SMILES: CCc1ccc(Br)cc1C1OC12C(=O)C(C)(C)OC2C]

To a solution of lithium diisopropylamide (0.12 mol) in anhydrous tetrahydrofuran (150 ml) at −70° C. is added a second solution of 4-bromo-2,2,5-trimethyl-4,5-dihydro-3(2H)-furanone (23.5 g, 0.11 mol) in anhydrous tetrahydrofuran (40 ml), at such a rate as to keep the internal temperature below −65° C. Once the addition is complete the reaction mixture is stirred at −70° C. for a further 20 minutes, followed by addition of 2-ethyl-5-bromobenzaldehyde (23.9 g, 0.11 mol) as a solution in anhydrous tetrahydrofuran (40 ml) drop-wise over 20 minutes. After further stirring at −70° C. for 20 minutes the reaction mixture is allowed to warm to room temperature then stirred for an additional 30 minutes. The reaction mixture is then quenched by pouring into ice/water (acidified to pH 3 with 2M hydrochloric acid) (500 ml) and extracted with ethyl acetate (3×100 ml). Organic fractions are combined, washed with water and brine, then dried over magnesium sulphate. The suspension is filtered, and the filtrate is concentrated in vacuo to afford a mixture of 2-(5-bromo-2-ethylphenyl)-4,6,6-trimethyl-1,5-dioxaspiro[2.4]heptan-7-one and 2-ethyl-5-bromobenzaldehyde (40.50 g), in an approximate 3:1 ratio. This material is used without purification in the next step.

1H NMR (CDCl$_3$): δ 7.47 (m, 1H), 7.41 (m, 1H), 7.10 (d, 1H), 4.47 (q, 1H), 4.39 (s, 1H), 2.60 (q, 2H), 1.38 (s, 3H), 1.35 (s, 3H), 1.23 (t, 3H), 0.70 (d, 3H).

Step 3: Preparation of 4-(5-Bromo-2-ethylphenyl)-2,2,6-trimethylpyran-3,5-dione

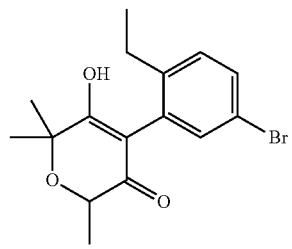 [SMILES: CCc1ccc(Br)cc1C1=C(O)C(C)(C)OC(C)C1=O]

To ice-cold concentrated sulphuric acid (50 ml) is added a solution of crude 2-(5-bromo-2-ethylphenyl)-4,6,6-trimethyl-1,5-dioxaspiro[2.4]heptan-7-one (40 g) in 1,2-dichloroethane (50 ml) over 20 minutes. After further stirring at 0° C. for 1 hour the reaction mixture is carefully poured into ice (500 g), and the two phases separated. The aqueous phase is further extracted with dichloromethane (2×100 ml), then all organic fractions are combined, washed with water, and concentrated under reduced pressure. The crude product is re-dissolved in ethyl acetate (500 ml), extracted into 0.5M aqueous potassium carbonate, and washed with additional ethyl acetate (×2). The aqueous phase is then carefully acidified with concentrated hydrochloric acid, and the product extracted with ethyl acetate (3×150 ml). Organic fractions are combined, washed with brine then dried over magnesium sulfate, filtered, and the filtrate concentrated in vacuo. The crude product is further purified by flash column chromatography to afford 4-(5-bromo-2-ethylphenyl)-2,2,6-trimethylpyran-3,5-dione (14.10 g) as a white foam.

1H NMR (CDCl$_3$): δ1.08 (m, 3H), 1.38-1.62 (m, 9H), 2.25 (m, 2H), 4.38 and 4.71 (m, 1H), 5.72 and 5.83 (2×br. s, 1H), 7.20 (m, 2H), 7.48 (m, 1H).

Example P3

4-(4'-Chloro-4-trifluoromethylbiphenyl-3-yl)-2,2,6,6-tetramethylpyran-3,5-dione

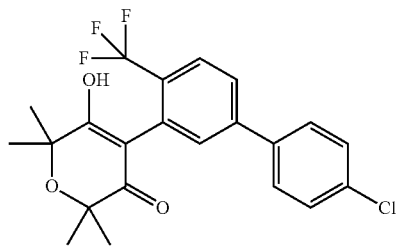 [SMILES: CC1(C)OC(C)(C)C(O)=C(c2cc(-c3ccc(Cl)cc3)ccc2C(F)(F)F)C1=O]

Step 1: Preparation of 4'-chloro-4-trifluoromethyl-biphenyl-3-carbaldehyde

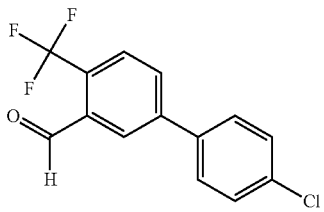 [SMILES: O=Cc1cc(-c2ccc(Cl)cc2)ccc1C(F)(F)F]

To a mixture of 3-chloro-6-trifluoromethylbenzaldehyde (1.0 g, 4.79 mmol), 4-chlorophenyl boronic acid (1.12 g, 7.19 mmol), potassium phosphate (2.03 g, 9.59 mmol), dicyclohexyl-(2',6'-dimethoxy-biphenyl-2-yl)-phosphane (0.079 g, 0.19 mmol) and palladium acetate (0.022 g, 0.096 mmol) is added degassed toluene (9 ml), then the mixture is further purged with nitrogen.

The suspension is next sealed then stirred at ambient temperature for 5 minutes, than heated at 160° C. for 1 hour under microwave irradiation. After cooling the reaction mixture is partitioned between 2M hydrochloric acid and dichloromethane, and the aqueous phase further extracted with dichloromethane (×2). The organic fractions are combined then evaporated under reduced pressure to yield a crude product which is purified by flash column chromatography (100% hexane to 10% ethyl acetate in hexanes as eluant) to afford 4'-chloro-4-trifluoromethyl-biphenyl-3-carbaldehyde (1.78 g) as an orange gum. This material is used directly in the next step.

Step 2: Preparation of 4-[1-(4'-chloro-4-trifluoromethylbiphenyl-3-yl)methylidene]-2,2,5,5-tetramethyldihydrofuran-3-one

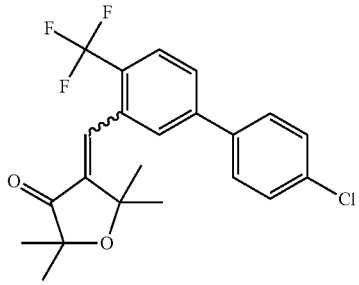 [SMILES: CC1(C)OC(C)(C)C(=Cc2cc(-c3ccc(Cl)cc3)ccc2C(F)(F)F)C1=O]

To an ice-cold solution of 2,2,5,5-tetramethyldihydrofuran-3-one (0.887 g, 6.25 mmoles) in 1,2-dimethoxyethane (10 ml) is added sodium methoxide (0.405 g, 7.50 mmoles) in one portion. The reaction mixture is stirred at 0° C. for 30 minutes, followed by the dropwise addition of 4'-chloro-4-trifluoromethylbiphenyl-3-carbaldehyde (1.779 g, 6.25 mmoles) as a solution in 1,2-dimethoxyethane (10 ml). The reaction mixture is stirred at 0° C. for 30 minutes and then at ambient temperature for a further 1 hour after which it is partitioned between 1M hydrochloric acid and dichloromethane. The aqueous phase is extracted again with dichloromethane, than all organics are combined and evaporated to afford 4-[1-(4'-chloro-4-trifluoromethylbiphenyl-3-yl)methylidene]-2,2,5,5-tetramethyldihydrofuran-3-one (2.50 g) as a yellow gum. This material is used directly in the next step.

Step 3: Preparation of 2-(4'-Chloro-4-trifluoromethylbiphenyl-3-yl)-4,4,6,6-tetramethyl-1,5-dioxaspiro[2.4]heptan-7-one

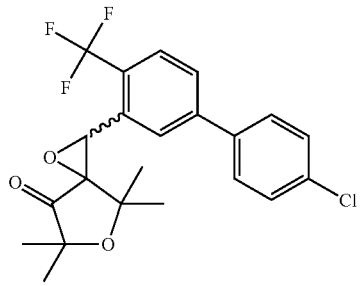 [SMILES: CC1(C)OC(C)(C)C2(OC2c2cc(-c3ccc(Cl)cc3)ccc2C(F)(F)F)C1=O]

To a solution of 4-[1-(4'-chloro-4-trifluoromethylbiphenyl-3-yl)methylidene]-2,2,5,5-tetramethyldihydrofuran-3-one (2.50 g, 6.12 mmol) in methanol (75 ml) at 35° C. is added 50% aqueous hydrogen peroxide solution (0.70 ml, 12.2 mmol), followed immediately by a solution of 2M aqueous lithium hydroxide (0.76 ml, 1.52 mmol). This mixture is stirred at 35° C. for 45 minutes, then allowed to cooled to room temperature and quenched with saturated sodium metabisulfite solution. The crude product is extracted with diethyl ether (×2), then all organics are combined and dried over magnesium sulfate. After filtration the filtrate is concentrated in vacuo to afford 2-(4'-chloro-4-trifluoromethylbiphenyl-3-yl)-4,4,6,6-tetramethyl-1,5-dioxaspiro[2.4]heptan-7-one (2.59 g) as a yellow gum. This material is used directly in the next step.

Step 4: Preparation of 4-(4'-Chloro-4-trifluoromethylbiphenyl-3-yl)-2,2,6,6-tetramethylpyran-3,5-dione

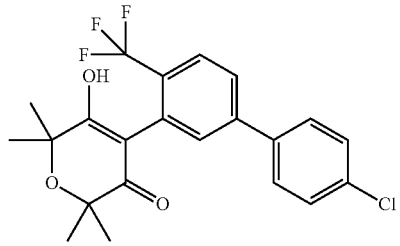 [SMILES: CC1(C)OC(C)(C)C(O)=C(c2cc(-c3ccc(Cl)cc3)ccc2C(F)(F)F)C1=O]

To an ice-cold solution of crude 2-(4'-chloro-4-trifluoromethylbiphenyl-3-yl)-4,4,6,6-tetramethyl-1,5-dioxaspiro[2.4]heptan-7-one (2.59 g, 6.12 mmoles) in dichloroethane (25 ml) is added concentrated sulfuric acid (5 ml), followed by stirring at this temperature for 2 hours. The reaction mixture is poured into ice, extracted with dichloromethane (×2), and the combined organics are evaporated under reduced pressure to yield a brown gum. Purification by flash column chromatography (isohexane to 30% ethyl acetate in isohexane as eluant) then reverse phase preparative HPLC affords 4-(4'-chloro-4-trifluoromethylbiphenyl-3-yl)-2,2,6,6-tetramethylpyran-3,5-dione (0.370 g) as a white solid.

1H NMR (CDCl$_3$): δ7.85 (d, 1H), 7.69 (d, 1H), 7.53 (d, 2H), 7.44 (d, 2H), 7.39 (s, 1H), 1.60 (app. d, 6H), 1.48 (s, 6H)

Example P4

Preparation of 4-(5-Bromo-2-iodophenyl)-2,2,6,6-tetramethylpyran-3,5-dione

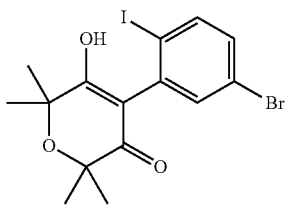 [SMILES: CC1(C)OC(C)(C)C(O)=C(c2cc(Br)ccc2I)C1=O]

Step 1: Preparation of 5-Bromo-2-iodobenzaldehyde

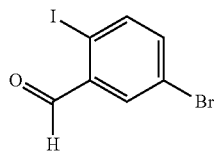

To a solution of 5-bromo-2-iodobenzonitrile (5.00 g, 16.00 mmoles) in anhydrous tetrahydrofuran (80 ml) at −80° C. is added diisobutyl aluminium hydride (16.0 ml, 16.0 mmoles, 1M solution in toluene) dropwise over 10 minutes. The reaction mixture is stirred at −80° C. for a 1 hour, then allowed to warm to ambient temperature and stir overnight. Additional diisobutyl aluminium hydride (16.0 ml, 16.0 mmoles, 1M solution in toluene) is next added dropwise at room temperature, and the reaction mixture further stirred for 1 hour. After careful quenching with 2M hydrochloric acid (cooling in ice bath), the crude product is extracted with ethyl acetate (×2), then all organics are combined and dried over magnesium sulfate and filtered. The filtrate is evaporated under reduced pressure then purified by flash column chromatography (isohexane to 10% ethyl acetate in isohexane eluant) to afford 5-bromo-2-iodobenzaldehyde (0.85 g).

Step 2: Preparation of 4-[1-(5-Bromo-2-iodophenyl)methylidene]-2,2,5,5-tetramethyldihydrofuran-3-one

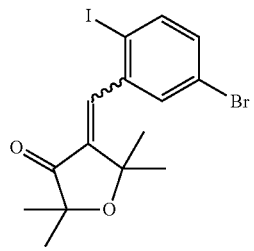 [SMILES: CC1(C)OC(C)(C)C(=Cc2cc(Br)ccc2I)C1=O]

To an ice-cold solution of 2,2,5,5-tetramethyldihydrofuran-3-one (0.388 g, 2.73 mmoles) in anhydrous 1,2-dimethoxyethane (5 ml) is added sodium methoxide (0.177 g, 3.27 mmoles) in one portion. The reaction mixture is stirred for 5 minutes at this temperature, followed by the dropwise addition of 5-bromo-2-iodo-benzaldehyde (0.850 g, 2.73 mmoles) as a solution in 1,2-dimethoxyethane (5 ml). The reaction mixture is further stirred at 0° C. for 30 minutes, then at ambient temperature for a 1 hour. After partitioning between 1M hydrochloric acid and dichloromethane, the organic phase is separated, and the aqueous phase is extracted again with additional dichloromethane. All organics are combined then concentrated in vacuo to afford 4-[1-(5-bromo-2-iodophenyl)methylidene]-2,2,5,5-tetramethyldihydrofuran-3-one (1.18 g) as a yellow gum.

Step 3: Preparation of 2-(5-Bromo-2-iodophenyl)-4,4,6,6-tetramethyl-1,5-dioxaspiro[2.4]heptan-7-one

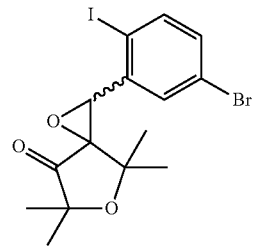 [SMILES: CC1(C)OC(C)(C)C2(OC2c2cc(Br)ccc2I)C1=O]

To a solution of 4-[1-(5-bromo-2-iodophenyl)methylidene]-2,2,5,5-tetramethyldihydrofuran-3-one (1.18 g, 2.73 mmol) in methanol (50 ml) at 35° C. is added 50% aqueous hydrogen peroxide solution (0.31 ml, 5.46 mmol), followed immediately by 2M aqueous lithium hydroxide (0.34 ml, 0.68 mmol). This mixture is stirred at 35° C. for 3 hours, then quenched with saturated aqueous sodium metabisulfite and extracted with dichloromethane. The organic phase is separated, and the aqueous phase extracted again with dichloromethane. All organics are combined then evaporated under reduced pressure to afford 2-(5-bromo-2-iodophenyl)-4,4,6,6-tetramethyl-1,5-dioxaspiro[2.4]heptan-7-one as an oil which is used directly in the next step.

Step 4: Preparation of 4-(5-Bromo-2-iodophenyl)-2,2,6,6-tetramethylpyran-3,5-dione

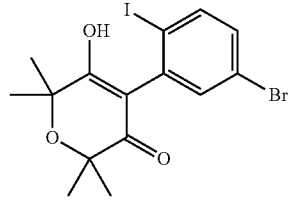 [SMILES: CC1(C)OC(C)(C)C(O)=C(c2cc(Br)ccc2I)C1=O]

To crude 2-(5-bromo-2-iodophenyl)-4,4,6,6-tetramethyl-1,5-dioxaspiro[2.4]heptan-7-one (from step 3) is added ice-cold concentrated sulphuric acid, and the reaction mixture is stirred at ambient temperature for 30 minutes. After dilution with distilled water the product is extracted with dichloromethane (×2), then the combined organics are evaporated under reduced pressure. Purification by flash column chromatography (20% ethyl acetate in isohexane to ethyl acetate as eluant) affords 4-(5-bromo-2-iodophenyl)-2,2,6,6-tetramethylpyran-3,5-dione (0.225 g) as a beige coloured solid.

1H NMR (CDCl₃): δ7.80 (d, 1H), 7.33 (m, 1H), 7.25 (m, 1H), 1.66 (s, 3H), 1.60 (s, 3H), 1.55 (s, 3H), 1.48 (s, 3H).

Example P5

Preparation of 4-(5-Bromo-2-trifluoromethoxyphenyl)-2,2,6,6-tetramethylpyran-3,5-dione

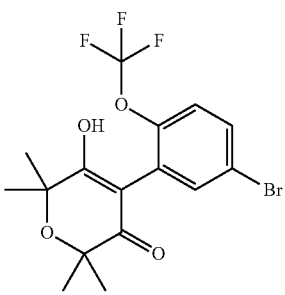 [SMILES: CC1(C)OC(C)(C)C(O)=C(c2cc(Br)ccc2OC(F)(F)F)C1=O]

Step 1: Preparation of 4-[1-(5-Bromo-2-trifluoromethoxyphenyl)-methylidene]-2,2,5,5-tetramethyldihydrofuran-3-one

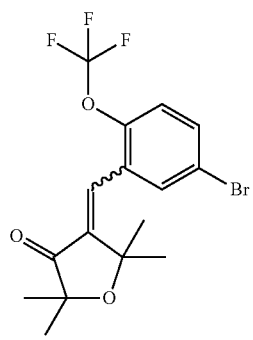

To an ice-cold solution of 2,2,5,5-tetramethyldihydrofuran-3-one (2.84 g, 20.00 mmol) in anhydrous 1,2-dimethoxyethane (6 ml) is added sodium methoxide (1.19 g, 22.04 mmol) in one portion. After stirring at this temperature for 5 minutes a solution of 5-bromo-2-trifluoromethoxybenzaldehyde (4.84 g, 18.00 mmol) in 1,2-dimethoxyethane (6 ml) is added dropwise over 10 mins, followed by stirring at 0° C. for a further 1 hour. After warming to room temperature the reaction mixture is diluted with ether and washed with 2M hydrochloric acid (×2). Organic fractions are combined, dried over magnesium sulphate, filtered and the filtrate evaporated in vacuo to afford 4-[1-(5-bromo-2-trifluoromethoxyphenyl)-methylidene]-2,2,5,5-tetramethyldihydrofuran-3-one (7.06 g) as an orange liquid.

Step 2: Preparation of 2-(5-Bromo-2-trifluoromethoxyphenyl)-4,4,6,6-tetramethyl-1,5-dioxaspiro[2.4]heptan-7-one

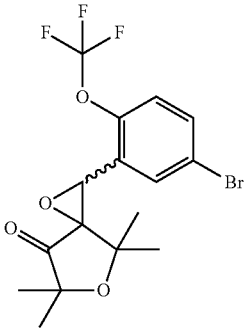 [SMILES: CC1(C)OC(C)(C)C2(OC2c2cc(Br)ccc2OC(F)(F)F)C1=O]

To a solution of 4-[1-(5-bromo-2-trifluoromethoxyphenyl)-methylidene]-2,2,5,5-tetramethyldihydrofuran-3-one (7.06 g, 18.00 mmol) in methanol (300 ml) at 35° C. is added 50% aqueous hydrogen peroxide (1.80 ml, 27.00 mmol), immediately followed by 2M aqueous lithium hydroxide (1.80 ml, 3.60 mmol). After stirring at this temperature for 1 hour the reaction mixture is allowed to cool, then quenched with 10% sodium metabisulfite solution (negative KI-starch indicator test). The reaction mixture is extracted with diethyl ether (×3), then the organic phase is further washed with saturated aqueous sodium bicarbonate (×2) then brine. All organics are combined, dried over magnesium sulfate, filtered and the filtrate concentrated in vacuo to afford 2-(5-bromo-2-trifluoromethoxyphenyl)-4,4,6,6-tetramethyl-1,5-dioxaspiro[2.4]heptan-7-one (6.34 g, 86%) as a yellow oil.

1H NMR (CDCl₃): δ 7.84 (s, 0.4H, isomer A), 7.56 (s, 0.6H, isomer B), 7.52 (d, 0.6H, isomer B), 7.48 (d, 0.4H, isomer A), 7.15 (d, 0.6H, isomer B), 7.07 (d, 0.4H, isomer A), 4.46 (m, 1H, isomers A and B), 1.47 (s, 1.2H, isomer A), 1.39-1.28 (m, 7.8H, isomers A and B), 1.12 (s, 1.2H, isomer A), 0.83 (s, 1.8H, isomer B)

Step 3: Preparation of 4-(5-Bromo-2-trifluoromethoxyphenyl)-2,2,6,6-tetramethylpyran-3,5-dione

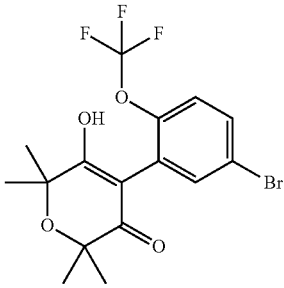 [SMILES: CC1(C)OC(C)(C)C(O)=C(c2cc(Br)ccc2OC(F)(F)F)C1=O]

To an ice-cold solution of concentrated sulphuric acid (10 ml) is added a second solution of 2-(5-bromo-2-trifluoromethoxyphenyl)-4,4,6,6-tetramethyl-1,5-dioxaspiro[2.4] heptan-7-one (6.34 g, 15.00 mmol) in 1,2-dichloroethane (10 ml) dropwise over 5 minutes. This biphasic mixture is stirred vigorously for 2 hours at 0° C., then poured into ice-water, rinsing with a small amount of additional 1,2-dichloroethane/ water. This mixture is then concentrated under vacuum to remove all organic solvents, until a free-flowing solid was produced. The solid is filtered, washed with water then isohexane, followed by drying under vacuum overnight. The solid is next redissolved in ethyl acetate, dried over magnesium sulfate, filtered and the filtrate concentrated in vacuo to afford 4-(5-bromo-2-trifluoromethoxyphenyl)-2,2,6,6-tetramethylpyran-3,5-dione (4.17 g, 68%).

1H NMR (CDCl$_3$): δ7.57 (dd, 1H), 7.24 (d, 2H), 1.52 (br.s, 12H).

Example P6

Preparation of 4-(4-Bromo-4'-chlorobiphenyl-3-yl)-2,2,6,6-tetramethylpyran-3,5-dione

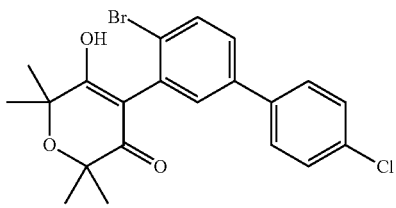 [SMILES: CC1(C)OC(C)(C)C(O)=C(c2cc(-c3ccc(Cl)cc3)ccc2Br)C1=O]

Step 1: Preparation of 4-Bromo-4'-chloro-biphenyl-3-carbaldehyde

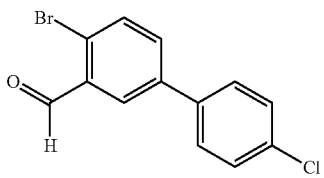 [SMILES: O=Cc1cc(-c2ccc(Cl)cc2)ccc1Br]

To a solution of 4-bromo-4'-chloro-3-iodobiphenyl (4.80 g, 0.012 mol) (described in WO 2008/071405) in anhydrous diethyl ether/tetrahydrofuran (120 ml, 1:1 ratio) at −75° C. is added isopropyl magnesium bromide (18.96 ml, 15% solution in tetrahydrofuran) dropwise such as to maintain an internal temperature below −70° C. Once addition is complete the reaction mixture is stirred at −75° C. for 2 hours, then warmed to −45° C. Anhydrous N,N-dimethylformamide (1.71 g, 0.0184 mol) is next added dropwise, maintaining temperature below −40° C., followed by warming to room temperature and quenching with 2M hydrochloric acid (60 ml). The reaction mixture is further diluted with diethyl ether, the two phases separated, and the aqueous phase extracted with additional diethyl ether. The combined organic extracts are washed with brine, dried over magnesium sulfate, filtered and the filtrate concentrated in vacuo. The crude product is purified by flash column chromatography (2% ethyl acetate in hexane eluant) to afford 4-bromo-4'-chloro-biphenyl-3-carbaldehyde (2.7 g, 75%) as a white solid.

Step 2: Preparation of 4-[1-(4-Bromo-4'-chlorobiphenyl-3-yl)-methylidene]-2,2,5,5-tetramethyldihydrofuran-3-one

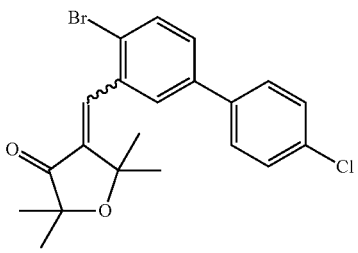 [SMILES: CC1(C)OC(C)(C)C(=Cc2cc(-c3ccc(Cl)cc3)ccc2Br)C1=O]

To an ice-cold solution of dihydro-2,2,5,5-tetramethylfuran-3-one (1.37 g (9.68 mmol) in anhydrous 1,2-dimethoxyethane (10 ml) is added sodium methoxide (0.575 g, 10.60 mmol) in one portion, followed by stirring at this temperature for 10 minutes. To this slurry is then added a second solution of 4-bromo-4'-chloro-biphenyl-3-carbaldehyde (2.60 g, 8.80 mmol) in 1,2-dimethoxyethane (10 ml) dropwise. When addition is complete the reaction mixture is stirred at 0° C. for a further 1 hour, then quenched with 2M hydrochloric acid (50 ml). After stirring for an additional 1 hour the solution is diluted with diethyl ether, the two phases separated, and the aqueous phase further extracted with diethyl ether (×2). The combined organics are further washed with brine, then dried over magnesium sulfate, filtered, and the filtrate concentrated in vacuo to afford 4-[1-(4-bromo-4'-chlorobiphenyl-3-yl)-methylidene]-2,2,5,5-tetramethyldihydrofuran-3-one (3.40 g, 92%) as a yellow gum.

Step 3: Preparation of 2-(4-Bromo-4'-chlorobiphenyl-3-yl)-4,4,6,6-tetramethyl-1,5-dioxaspiro[2.4]heptan-7-one

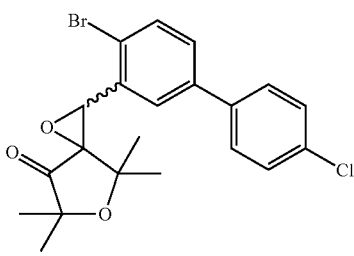 [SMILES: CC1(C)OC(C)(C)C2(OC2c2cc(-c3ccc(Cl)cc3)ccc2Br)C1=O]

To a solution of 4-[1-(4-bromo-4'-chlorobiphenyl-3-yl)-methylidene]-2,2,5,5-tetramethyldihydrofuran-3-one (3.40 g, 9.03 mmol) in methanol (140 ml) at 35° C. is added 50% aqueous hydrogen peroxide (1.04 ml, 15.60 mmol), immediately followed by 2M aqueous lithium hydroxide (1.15 ml, 2.30 mmol). The reaction mixture is stirred for a further 45 minutes at 35° C., then allowed to cool to room temperature and quenched with saturated sodium metabisulfite. After extracting the product into diethyl ether (×3) the organic phase is separated, washed with additional water, then dried over magnesium sulfate. After filtration the filtrate is concentrated in vacuo to afford 2-(4-bromo-4'-chlorobiphenyl-3-yl)-

4,4,6,6-tetramethyl-1,5-dioxaspiro[2.4]heptan-7-one (3.0 g) as a yellow solid. This material was of sufficient purity to use directly in the next step.

Step 4: Preparation of 4-(4-Bromo-4'-chlorobiphenyl-3-yl)-2,2,6,6-tetramethylpyran-3,5-dione

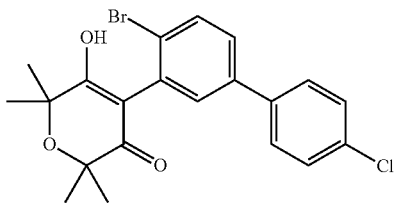 [SMILES: CC1(C)OC(C)(C)C(O)=C(c2cc(-c3ccc(Cl)cc3)ccc2Br)C1=O]

To an ice-cold solution of 2-(4-bromo-4'-chlorobiphenyl-3-yl)-4,4,6,6-tetramethyl-1,5-dioxaspiro[2.4]heptan-7-one (3.00 g, 6.90 mmol) in dichloromethane (3.5 ml) is added concentrated sulphuric acid (6.5 ml) at such a rate as maintain an internal temperature below 5° C. After the addition is completed the reaction mixture is stirred for a further 20 minutes, after which distilled water (25 ml) is added dropwise at 0° C. The reaction mixture is maintained at 5-10° C. for 5 minutes, then concentrated in vacuo to remove organic solvents. The aqueous phase is filtered and the resulting solid triturated with hexane to afford 4-(4-bromo-4'-chlorobiphenyl-3-yl)-2,2,6,6-tetramethylpyran-3,5-dione (2.56 g, 85%).
NMR (CDCl$_3$): δ7.75 (d, 1H), 7.49 (d, 2H), 7.45 (dd, 1H), 7.40 (s, 2H), 7.36 (s, 1H), 5.56 (br.s, 1H), 1.65 (s, 3H), 1.58 (s, 3H), 1.53 (s, 3H), 1.47 (s, 3H).

Example P7

Preparation of 4-(5-Bromo-2-fluorophenyl)-2,2,6,6-tetramethylpyran-3,5-dione

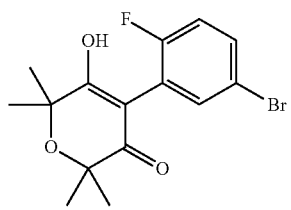

Step 1: Preparation of 4-[1-(5-Bromo-2-fluorophenyl)-methylidene]-2,2,5,5-tetramethyldihydrofuran-3-one

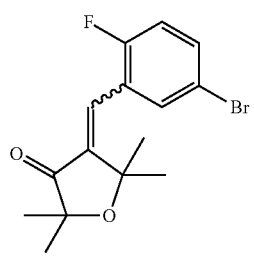

To an ice-cold solution of dihydro-2,2,5,5-tetramethylfuran-3-one (4.56 g, 32.10 mmol) in anhydrous 1,2-dimethoxyethane (25 ml) is added sodium methoxide (1.91 g, 35.10 mol) in one portion. After stirring at room temperature for 10 minutes a second solution of 5-bromo-2-fluorobenzaldehyde (5.93 g, 29.10 mmol) in anhydrous 1,2-dimethoxyethane (45 ml) is added dropwise, followed by stirring at 0° C. for a further 45 minutes. The reaction mixture is quenched with 2M hydrochloric acid (50 ml), then diluted with diethyl ether and the two phases separated. The aqueous phase is further extracted with diethyl ether (×2), then all organics are combined, washed with brine and dried over magnesium sulfate. After filtration the filtrate is concentrated in vacuo to afford 4-[1-(5-bromo-2-fluorophenyl)-methylidene]-2,2,5,5-tetramethyldihydrofuran-3-one (9.30 g, 96%) as a yellow gum.

Step 2: Preparation of 2-(5-Bromo-2-fluorophenyl)-4,4,6,6-tetramethyl-1,5-dioxaspiro[2.4]heptan-7-one

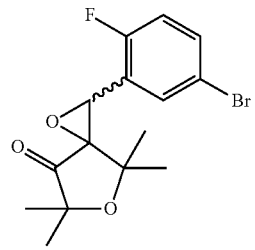

To a solution of 4-[1-(5-bromo-2-fluorophenyl)-methylidene]-2,2,5,5-tetramethyldihydrofuran-3-one (9.30 g, 29.00 mmol) in methanol (280 ml) at 35° C. is added 50% aqueous hydrogen peroxide (3.36 ml, 50.40 mmol), followed immediately by 2M aqueous lithium hydroxide (3.68 ml, 7.36 mmol). Stirring is continued at this temperature for 1 hour, then the reaction mixture is allowed to cool to room temperature, then quenched with saturated sodium metabisulfite (100 ml) and extracted with ether (×3). Organics are combined, dried over magnesium sulfate, then filtered and the filtrate concentrated in vacuo to afford 2-(5-bromo-2-fluorophenyl)-4,4,6,6-tetramethyl-1,5-dioxaspiro[2.4]heptan-7-one (6.60 g, 68%) as a yellow gum.

Step 3: Preparation of 4-(5-Bromo-2-fluorophenyl)-2,2,6,6-tetramethylpyran-3,5-dione

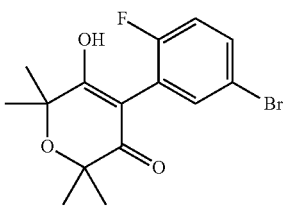 [SMILES: CC1(C)OC(C)(C)C(O)=C(c2cc(Br)ccc2F)C1=O]

To a solution of 2-(5-bromo-2-fluorophenyl)-4,4,6,6-tetramethyl-1,5-dioxaspiro[2.4]heptan-7-one (6.60 g, 19.30 mmol) in dichloromethane (8 ml) is added a second ice-cold solution of concentrated sulphuric acid (13.8 ml) dropwise, maintaining temperature below 5° C. The reaction mixture is stirred for a further 30 minutes, then quenched with distilled water (50 ml). After stirring for an additional 10 minutes the organics are removed in vacuo, and the resulting precipitate is filtered then triturated with water. After washing with hexanes the solid is dried to afford 4-(5-bromo-2-fluorophenyl)-2,2,6,6-tetramethylpyran-3,5-dione (4.30 g, 65%).

1H NMR (CDCl$_3$): δ7.5 (m, 1H), 7.34 (m, 1H), 7.06 (m, 1H), 5.69 (br. s, 1H), 1.56 (d, 6H), 1.52 (d, 6H).

Example P8

Preparation of 4-(4'-Chloro-4-cyclopropyl-2'-fluoro-biphenyl-3-yl)-2,2,6,6-tetramethylpyran-3,5-dione

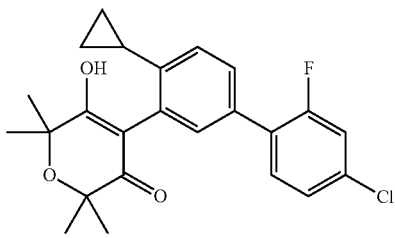 [SMILES: CC1(C)OC(C)(C)C(O)=C(c2cc(-c3ccc(Cl)cc3F)ccc2C2CC2)C1=O]

Step 1: Preparation of 4'-chloro-2'-fluoro-4-hydroxy-biphenyl-3-carbaldehyde

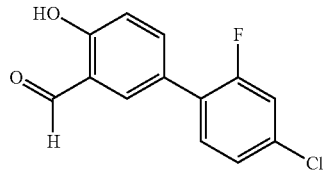 [SMILES: O=Cc1cc(-c2ccc(Cl)cc2F)ccc1O]

To a mixture of 5-bromosalicyaldehyde (30.0 g, 0.15 mol), 2-fluoro-4-chlorophenylboronic acid (30.0 g, 0.17 mol) and sodium carbonate (24.0 g, 0.23 mol) is added 1,2-dimethoxy-ethane (225 ml) and distilled water (75 ml), and the suspension is stirred under a nitrogen atmosphere. To this mixture is then added [1,1'-bis(diphenylphosphino)ferrocene]palladium(II)chloride (4.5 g, 7.5 mmol), followed by heating at reflux overnight. After cooling to room temperature and dilution with distilled water (500 ml) and dichloromethane (500 ml), the two phases are separated, and the aqueous phase extracted again with dichloromethane (2×500 ml). Organic fractions are combined, washed with brine (800 ml) then dried over magnesium sulphate. The suspension is filtered and the filtrate is concentrated in vacuo. Then crude material is purified by flash column purification (5-10% ethyl acetate in isohexane eluant) to afford 4'-chloro-2'-fluoro-4-hydroxy-biphenyl-3-carbaldehyde (33.61 g, 89%) as a pale yellow solid.

Step 2: Preparation of Trifluoromethanesulfonic acid 4'-chloro-2'-fluoro-3-formylbiphenyl-4-yl ester

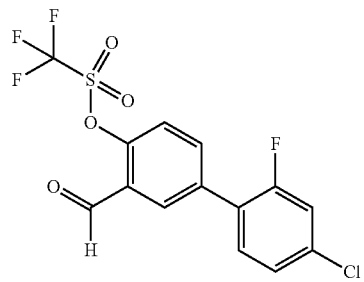 [SMILES: O=Cc1cc(-c2ccc(Cl)cc2F)ccc1OS(=O)(=O)C(F)(F)F]

To an ice-cold mixture of 4'-chloro-2'-fluoro-4-hydroxybi-phenyl-3-carbaldehyde (33.60 g, 0.13 mol) and pyridine (31.0 ml, 0.36 mol) in anhydrous dichloromethane (700 ml) is added triflic anhydride (27.0 ml, 0.16 mmol) dropwise over 30 minutes, maintaining temperature below 10° C. The reaction mixture is then allowed to warm to room temperature, followed by stirring overnight. After dilution with distilled water (500 ml) and dichloromethane (500 ml), the two layers are separated and the aqueous phase is extracted again with dichloromethane (2×500 ml). Organic fractions are combined, washed with brine (800 ml), then dried over magnesium sulfate and concentrated in vacuo. The crude product is purified by flash column chromatography (10% ethyl acetate in hexane eluant) to afford trifluoromethanesulfonic acid 4'-chloro-2'-fluoro-3-formylbiphenyl-4-yl ester as a yellow oil.

Step 3: Preparation of 4'-Chloro-4-cyclopropyl-2'-fluorobiphenyl-3-carbaldehyde

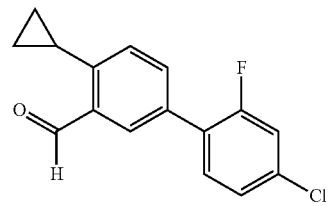

To a mixture of trifluoromethanesulfonic acid 4'-chloro-2'-fluoro-3-formylbiphenyl-4-yl ester (30.0 g, 0.078 mol), cyclopropyl boronic acid (8.80 g, 0.10 mol), potassium phosphate (58.40 g, 0.28 mol) and sodium bromide (8.0 g, 0.078 mol) is added toluene (300 ml) then distilled water (30 ml) under a nitrogen atmosphere. To this mixture is then added tetrakis(triphenylphosphine) palladium (9.60 g, 8.40 mmol) in one portion, and the mixture is then heated at 100° C. overnight. After cooling to room temperature the mixture is diluted with distilled water (500 ml) and ethyl acetate (500 ml), and the two layers are separated and the aqueous phase extracted again with ethyl acetate (2×500 ml). Organic fractions are combined, washed with distilled water (1 L) then brine (1 L), and then dried over magnesium sulphate. The suspension is filtered and the filtrate concentrated in vacuo. The crude product is purified by flash column chromatography on silica gel, then additionally by flash column chromatography on basic alumina (10% ethyl acetate in hexane as eluant) to afford 4'-chloro-4-cyclopropyl-2'-fluoro-biphenyl-3-carbaldehyde (7.6 g, 36%).

Step 4: 4-[1-(4'-Chloro-4-cyclopropyl-2'-fluorobiphenyl-3-yl)methylidene]-2,2,5,5-tetramethyldihydrofuran-3-one

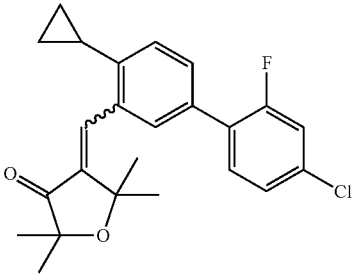 [SMILES: CC1(C)OC(C)(C)C(=Cc2cc(-c3ccc(Cl)cc3F)ccc2C2CC2)C1=O]

To an ice-cold solution of dihydro-2,2,5,5-tetramethylfuran-3-one (8.40 g, 0.059 mol) in anhydrous 1,2-dimethoxyethane (75 ml) is added sodium methoxide (3.60 g, 0.066 mol) in one portion, and the mixture is stirred at this temperature for 30 minutes. A solution of 4'-chloro-4-cyclopropyl-2'-fluorobiphenyl-3-carbaldehyde (14.80 g, 0.054 mmol) is then added dropwise over 20 minutes, maintaining temperature below 10° C. The reaction mixture is stirred at this temperature for 1 hour, then allowed to warm to room temperature before diluting with diethyl ether and distilled water. The two phases are separated, and the aqueous phase is extracted again with diethyl ether (×2). Organic fractions are combined, washed with brine, then dried over magnesium sulfate. The suspension is filtered and the filtrate concentrated in vacuo to afford 4-[1-(4'-chloro-4-cyclopropyl-2'-fluorobiphenyl-3-yl)methylidene]-2,2,5,5-tetramethyldihydrofuran-3-one (19.80 g) which is of sufficient purity to use directly in the next step.

Step 5: 2-(4'-Chloro-4-cyclopropyl-2'-fluorobiphenyl-3-yl)-4,4,6,6-tetramethyl-1,5-dioxa-spiro[2.4]heptan-7-one

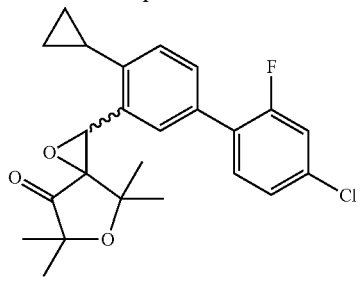

To a solution of 4-[1-(4'-chloro-4-cyclopropyl-2'-fluorobiphenyl-3-yl)methylidene]-2,2,5,5-tetramethyldihydrofuran-3-one (19.80 g, 0.050 mol) in methanol (830 ml) at 35° C. is added 50% aqueous hydrogen peroxide (5.00 ml, 0.075 mmol), followed immediately by 2M lithium hydroxide (5.00 ml, 0.01 mol) solution. The mixture is stirred at this temperature for a further 2 hours, then allowed to cool to room temperature. Then reaction mixture is quenched with 10% sodium metabisulfite (negative KI-starch indicator test) then diluted with diethyl ether. Most of the methanol is removed under vacuum, and the crude mixture is partitioned between distilled water and diethyl ether. The aqueous phase is further extracted with diethyl ether (×2), then all organics are combined and washed with saturated sodium bicarbonate (×2) then brine. After anhydrousing over magnesium sulfate the suspension is filtered and the filtrate concentrated in vacuo to afford 2-(4'-chloro-4-cyclopropyl-2'-fluorobiphenyl-3-yl)-4,4,6,6-tetramethyl-1,5-dioxa-spiro[2.4]heptan-7-one (18.2 g) as an orange foam. This material is of sufficient purity to use directly in the next step without further purification.

1H NMR (CDCl$_3$): δ 7.48 (s, 1H), 7.39 (d, 1H), 7.32 (t, 1H), 7.24-7.12 (m, 2H), 7.00 (d, 1H), 4.76 (s, 1H), 1.84-1.76 (m, 1H), 1.42-1.26 (m, 9H), 1.11-0.96 (m, 2H), 0.88-0.79 (m, 4H), 0.78-0.71 (m, 1H).

Step 6: Preparation of 4-(4'-Chloro-4-cyclopropyl-2'-fluorobiphenyl-3-yl)-2,2,6,6-tetramethylpyran-3,5-dione

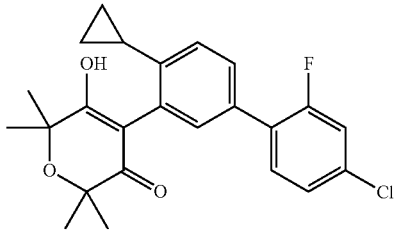 [SMILES: CC1(C)OC(C)(C)C(O)=C(c2cc(-c3ccc(Cl)cc3F)ccc2C2CC2)C1=O]

To a mixture of 2-(4'-chloro-4-cyclopropyl-2'-fluorobiphenyl-3-yl)-4,4,6,6-tetramethyl-1,5-dioxaspiro[2.4]heptan-7-one (18.20 g, 0.044 mol) and ytterbium triflate (2.40 g, 4.40 mmol) is added a solution of 5M lithium perchlorate (prepared from 46 ml diethyl ether and 24.40 g lithium perchlorate). The resulting suspension is stirred at room temperature for 3 days, then is diluted with diethyl ether (85 ml) and additional ytterbium triflate (7.80 g, 0.014 mol) is added. After stirring at room temperature for a further 3 days additional ytterbium triflate (13.63 g, 0.025 mol) is added, and the reaction mixture is stirred for 11 days. Finally, extra lithium perchlorate (24.40 g, 0.23 mol) is added in one portion, and the mixture is heated at 27° C. (internal temperature) for 1 day. The reaction mixture is partitioned between diethyl ether and distilled water, the two phases separated, and the aqueous phase is extracted with diethyl ether (×2). The organic fractions are combined, washed with brine then dried over magnesium sulphate. The suspension is filtered and the filtrate concentrated in vacuo. The crude material purified by flash column chromatography (10% ethyl acetate in hexanes as eluant) to afford an oil which is triturated with hexanes to afford 4-(4'-chloro-4-cyclopropyl-2'-fluorobiphenyl-3-yl)-2,2,6,6-tetramethylpyran-3,5-dione (4.78 g) as a white solid.

1H NMR (CDCl$_3$): δ 7.47 (d, 1H), 7.38 (t, 1H), 7.23 (s, 1H), 7.21-7.12 (m, 3H), 5.68 (s, 1H), 1.75 (m, 1H), 1.62 (s, 6H), 1.49 (s, 6H), 0.92-0.82 (m, 2H), 0.81-0.75 (m, 1H), 0.61-0.53 (m, 1H)

Example P9

Preparation of 4-(2',4'-Dichloro-4-cyclopropylbiphenyl-3-yl)-2,2,6,6-tetramethylpyran-3,5-dione

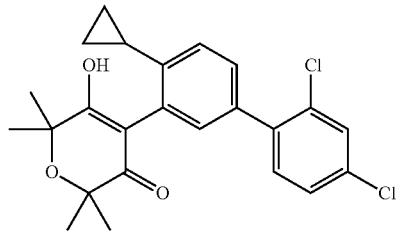 [SMILES: CC1(C)OC(C)(C)C(O)=C(c2cc(-c3ccc(Cl)cc3Cl)ccc2C2CC2)C1=O]

Step 1: Preparation of 2',4'-Dichloro-4-hydroxybiphenyl-3-carbaldehyde

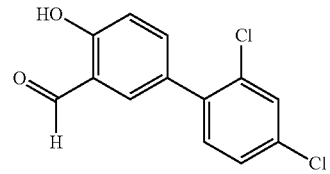 [SMILES: O=Cc1cc(-c2ccc(Cl)cc2Cl)ccc1O]

To a mixture of 5-bromosalicyaldehyde (30.0 g, 0.15 mol), 2,4-dichlorophenylboronic acid (32.0 g, 0.17 mol) and sodium carbonate (24.0 g, 0.23 mol) is added 1,2-dimethoxyethane (225 ml) and distilled water (75 ml), and the suspension is stirred under a nitrogen atmosphere. To this mixture is then added [1,1'-bis(diphenylphosphino)ferrocene]palladium(II)chloride (4.5 g, 7.5 mmol), followed by heating at reflux overnight. After cooling to room temperature and dilution with distilled water (500 ml) and dichloromethane (500 ml), the two phases are separated, and the aqueous phase extracted again with dichloromethane (2×500 ml). Organic fractions are combined, washed with brine (800 ml) then dried over magnesium sulphate. The suspension is filtered and the filtrate concentrated in vacuo. Then crude material is finally purified by flash column purification (10% ethyl acetate in isohexane eluant) to afford 2',4'-dichloro-4-hydroxybiphenyl-3-carbaldehyde (32.73 g, 82%) as a pale yellow solid.

Step 2: Preparation of Trifluoromethanesulfonic acid 2',4'-dichloro-3-formylbiphenyl-4-yl ester

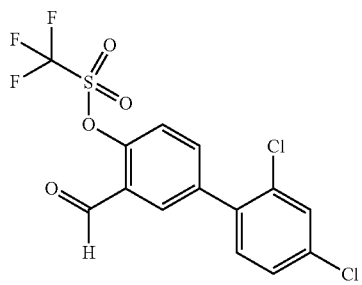

To an ice-cold mixture of 2',4'-dichloro-4-hydroxybiphenyl-3-carbaldehyde (31.70 g, 0.12 mol) and pyridine (25.0 ml, 0.29 mol) in anhydrous dichloromethane (650 ml) is added triflic anhydride (22.0 ml, 0.13 mmol) dropwise over 30 minutes, maintaining temperature between 0-10° C. The reaction mixture is then allowed to warm to room temperature, followed by stirring overnight. After dilution with distilled water (500 ml) and dichloromethane (300 ml), the two layers are separated and the organic phase is further washed with saturated aqueous copper sulfate solution (3×500 ml), water (500 ml), then brine (500 ml). After anhydrousing over magnesium sulfate the solvent is removed under vacuum and the crude product is purified by flash column chromatography (10% ethyl acetate in hexane eluant) to afford trifluoromethanesulfonic acid 2',4'-dichloro-3-formylbiphenyl-4-yl ester as an orange oil.

Step 3: Preparation of 2',4'-Dichloro-4-cyclopropyl-biphenyl-3-carbaldehyde

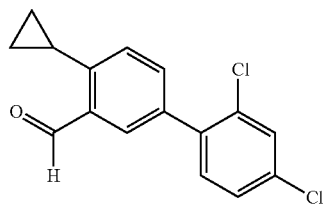 [SMILES: O=Cc1cc(-c2ccc(Cl)cc2Cl)ccc1C1CC1]

To a mixture of trifluoromethanesulfonic acid 2',4'-dichloro-3-formylbiphenyl-4-yl ester (30.0 g, 0.075 mol), cyclopropyl boronic acid (8.50 g, 0.097 mol), potassium phosphate (56.30 g, 0.27 mol) and sodium bromide (7.7 g, 0.075 mol) is added toluene (300 ml) then distilled water (30 ml) under a nitrogen atmosphere. To this mixture is then added tetrakis(triphenylphosphine) palladium (9.30 g, 0.0081 mol) in one portion, and the mixture is then heated at 100° C. overnight. After cooling to room temperature the mixture is diluted with distilled water (500 ml) and ethyl acetate (500 ml), and the two layers are separated. The aqueous phase is extracted again with ethyl acetate (2×500 ml), then all organic fractions are combined, then washed with distilled water (1 L) then brine (1 L). After drying over magnesium sulfate the suspension is filtered and the filtrate is concentrated in vacuo. The crude product is purified by flash column chromatography on silica gel (2-10% ethyl acetate in hexanes as eluant), then additionally by flash column chromatography on basic alumina (10% ethyl acetate in hexane as eluant) to afford 2',4'-dichloro-4-cyclopropylbiphenyl-3-carbaldehyde (11.7 g, 54%).

Step 4: 4-[1-(2',4'-Dichloro-4-cyclopropylbiphenyl-3-yl)-methylidene]-2,2,5,5-tetramethyldihydrofuran-3-one

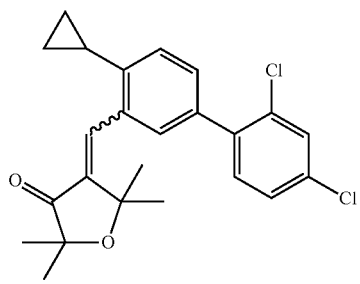 [SMILES: CC1(C)OC(C)(C)C(=Cc2cc(-c3ccc(Cl)cc3Cl)ccc2C2CC2)C1=O]

To an ice-cold solution of dihydro-2,2,5,5-tetramethylfuran-3-one (15.70 g, 0.11 mol) in anhydrous 1,2-dimethoxyethane (285 ml) is added sodium methoxide (6.50 g, 0.12 mol) in one portion, and the mixture is stirred at this temperature for 30 minutes. A solution of 2',4'-dichloro-4-cyclopropylbiphenyl-3-carbaldehyde (13.70 g, 0.047 mmol) is then added dropwise over 20 minutes, maintaining temperature below 10° C. The reaction mixture is stirred at this temperature for 2 hours, then allowed to warm to room temperature before diluting with diethyl ether and distilled water. The two phases are separated, and the aqueous phase is extracted again with diethyl ether (×2). Organic fractions are combined, washed with brine, then dried over magnesium sulphate. The suspension is filtered and filtrate concentrated in vacuo. The aqueous phase is further acidified with 2M hydrochloric acid then extracted again with diethyl ether (×2), dried over magnesium sulfate and concentrated in vacuo. All organics are combined, then diluted with toluene and azeotroped (×4) to afford 4-[1-(2',4'-dichloro-4-cyclopropylbiphenyl-3-yl)-methylidene]-2,2,5,5-tetramethyldihydrofuran-3-one (20.0 g) which is of sufficient purity to use directly in the next step.

Step 5: 2-(2',4'-Dichloro-4-cyclopropylbiphenyl-3-yl)-4,4,6,6-tetramethyl-1,5-dioxa-spiro[2.4]heptan-7-one

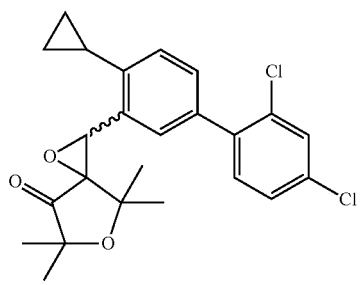 [SMILES: CC1(C)OC(C)(C)C2(OC2c2cc(-c3ccc(Cl)cc3Cl)ccc2C2CC2)C1=O]

To a solution of 4-[1-(2',4'-dichloro-4-cyclopropylbiphenyl-3-yl)-methylidene]-2,2,5,5-tetramethyldihydrofuran-3-one (20.0 g, 0.048 mol) in methanol (800 ml) at 35° C. is added 50% aqueous hydrogen peroxide (4.80 ml, 0.072 mmol), followed immediately by 2M lithium hydroxide (4.80 ml, 9.60 mmol) solution. The mixture is stirred at this temperature for a further 2 hours, then allowed to cool to room temperature. Then reaction mixture is quenched with 10% sodium metabisulfite (negative KI-starch indicator test) then diluted with diethyl ether. Most of the methanol is removed under vacuum, and the crude mixture is partitioned between distilled water and diethyl ether. The aqueous phase is further extracted with diethyl ether (×2), then all organics are combined and washed with saturated sodium bicarbonate (×2) then brine. After drying over magnesium sulfate the suspension is filtered and the filtrate concentrated in vacuo to afford 2-(2',4'-dichloro-4-cyclopropylbiphenyl-3-yl)-4,4,6,6-tetramethyl-1,5-dioxa-spiro[2.4]heptan-7-one (17.80 g) as an orange foam. This material is of sufficient purity to use directly in the next step without further purification.

1H NMR (CDCl$_3$): δ 7.49 (s, 1H), 7.37 (s, 1H), 7.37-7.25 (m, 2H), 7.20 (d, 1H), 6.99 (d, 1H), 4.75 (s, 1H), 1.80 (m, 1H), 1.40-1.28 (m, 9H), 1.10-0.98 (m, 2H), 0.90-0.80 (m, 4H), 0.75-0.80 (m, 1H).

Step 6: Preparation of 4-(2',4'-Dichloro-4-cyclopropylbiphenyl-3-yl)-2,2,6,6-tetramethylpyran-3,5-dione

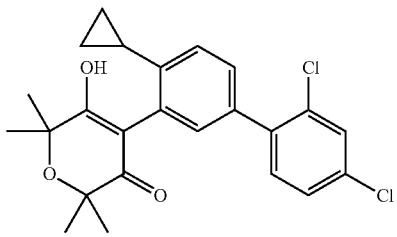 [SMILES: CC1(C)OC(C)(C)C(O)=C(c2cc(-c3ccc(Cl)cc3Cl)ccc2C2CC2)C1=O]

To a mixture of 2-(2',4'-dichloro-4-cyclopropylbiphenyl-3-yl)-4,4,6,6-tetramethyl-1,5-dioxa-spiro[2.4]heptan-7-one (17.80 g, 0.041 mol) and ytterbium triflate (2.20 g, 4.41 mmol) is added a solution of 5M lithium perchlorate (prepared from 42 ml diethyl ether and 22.30 g lithium perchlorate). The resulting suspension is stirred at room temperature for 17 days, at which stage further diethyl ether (42 ml), lithium perchlorate (22.3 g, 0.21 mol) and ytterbium triflate (19.8 g, 0.035 mol) is added. The reaction mixture is then heated at 27° C. (internal temperature) for 1 day, followed by partitioning between diethyl ether and distilled water. The two phases are separated, the aqueous phase is extracted with diethyl ether (×2), and then all organic fractions are combined, washed with brine then dried over magnesium sulphate. The suspension is filtered and the filtrate is concentrated in vacuo. The crude material is purified by flash column chromatography (ethyl acetate/hexane eluant) to give an oil which is triturated with hexanes to afford 4-(2',4'-dichloro-4-cyclopropylbiphenyl-3-yl)-2,2,6,6-tetramethylpyran-3,5-dione (2.80 g) as a white solid.

1H NMR (CDCl$_3$): δ 7.48 (s, 1H), 7.38 (dd, 1H), 7.29 (s, 2H), 7.16-7.11 (m, 2H), 5.69 (s, 1H), 1.76 (m, 1H), 1.61 (d, 6H), 1.49 (d, 6H), 0.92-0.86 (m, 2H), 0.82-0.76 (m, 1H), 0.62-0.54 (m, 1H).

Example P10

Preparation of 4-(2',4'-Dichloro-4-ethylbiphenyl-3-yl)-2,2,6,6-tetramethylpyran-3,5-dione

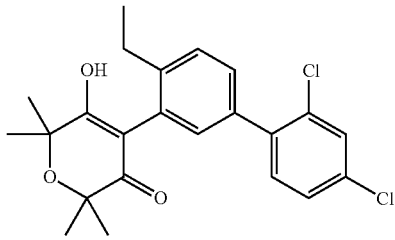 [SMILES: CCc1ccc(-c2ccc(Cl)cc2Cl)cc1C1=C(O)C(C)(C)OC(C)(C)C1=O]

Step 1: Preparation of 2',4'-Dichloro-4-ethylbiphenyl-3-carbaldehyde

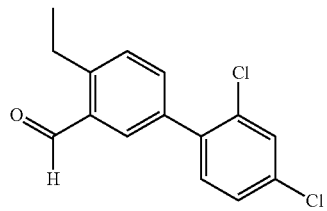 [SMILES: CCc1ccc(-c2ccc(Cl)cc2Cl)cc1C=O]

A suspension of 5-bromo-2-ethylbenzaldehyde (1.0 g, 4.7 mmol), 2,4-dichlorophenyl boronic acid (1.34 g, 7.0 mmol) and sodium carbonate (0.99 g, 7.98 mmol) in a mixed solvent system of 1,2-dimethoxyethane (12 ml) and distilled water (4 ml) is stirred under a nitrogen atmosphere, then flushed with nitrogen (×2). [1,1'-Bis(diphenylphosphino)ferrocene]palladium(II)chloride (1.15 g, 1.41 mmol) is then added in one portion and the suspension is again flushed with nitrogen, then heated at reflux overnight. After cooling to room temperature the reaction mixture is diluted with distilled water (10 ml) and extracted with dichloromethane (10 ml). The aqueous phase is extracted again with dichloromethane (×2), and the combined organic fractions are finally washed with brine then dried over magnesium sulfate. The crude product is purified by flash column chromatography (isohexane to 75:25 isohexane/ethyl acetate ratio eluant) to afford 2',4'-dichloro-4-ethylbiphenyl-3-carbaldehyde as a yellow oil.

Step 2: Preparation of 4-[1-(2',4'-Dichloro-4-ethylbiphenyl-3-yl)-methylidene]-2,2,5,5-tetramethyldihydrofuran-3-one

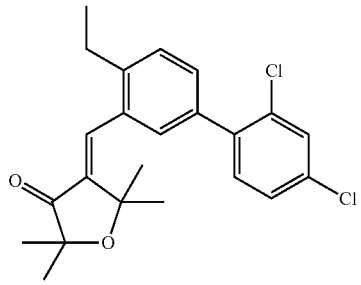 [SMILES: CCc1ccc(-c2ccc(Cl)cc2Cl)cc1/C=C1/C(=O)C(C)(C)OC1(C)C]

To an ice-cold solution of 2,2,5,5-tetramethyldihydrofuran-3-one (1.15 g, 0.0081 mol) in 1,2-dimethoxyethane (2 ml) is added sodium methoxide (0.481 g, 0.0089 mol) in one portion. The reaction mixture is then stirred for 5 minutes at this temperature, followed by the addition of a second solution of 2',4'-dichloro-4-ethylbiphenyl-3-carbaldehyde (2.02 g, 0.0072 mol) in 1,2-dimethoxyethane (2.7 ml). After stirring for an additional 2 hours at 0° C. the reaction mixture is allowed to stand at room temperature overnight. The crude solution is poured into 2M hydrochloric acid and extracted with ether (×3). The organics are combined, washed with brine, dried over magnesium sulfate and concentrated in vacuo. The residue is purified by flash column chromatography (5% ethyl acetate in isohexane to 25% ethyl acetate in isohexane) to afford 4-[1-(2',4'-dichloro-4-ethylbiphenyl-3-yl)-methylidene]-2,2,5,5-tetramethyldihydrofuran-3-one as a yellow gum.

Step 3A: Preparation of 2-(2',4'-Dichloro-4-ethylbiphenyl-3-yl)-4,4,6,6-tetramethyl-1,5-dioxaspiro[2.4]heptan-7-one

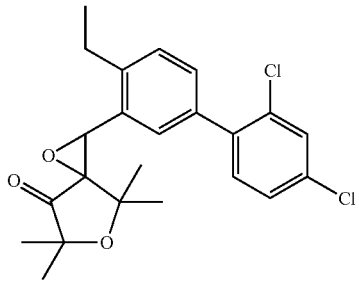 [SMILES: CCc1ccc(-c2ccc(Cl)cc2Cl)cc1C1OC12C(=O)C(C)(C)OC2(C)C]

To a solution of 4-[1-(2',4'-dichloro-4-ethylbiphenyl-3-yl)-methylidene]-2,2,5,5-tetramethyldihydrofuran-3-one (2.04 g, 0.0051 mol) in methanol (24 ml) at 55° C. is added hydrogen peroxide solution (0.43 ml, 0.0076 mmol, 50% wt solution), followed immediately by aqueous lithium hydroxide (0.25 ml, 0.0005 mol). The reaction mixture is heated at this temperature for 30 minutes, then is rapidly cooled to room temperature and quenched with saturated sodium thiosulphate. The crude product is extracted with diethyl ether (×3), washed with saturated sodium bicarbonate, then dried over magnesium sulfate. The residue is purified by flash column chromatography (5% ethyl acetate in isohexane to 25% ethyl acetate in isohexane) to afford 2-(2',4'-dichloro-4-ethylbiphenyl-3-yl)-4,4,6,6-tetramethyl-1,5-dioxaspiro[2.4]heptan-7-one as a yellow gum.

Step 3B: Preparation of 2-(2',4'-Dichloro-4-ethylbiphenyl-3-yl)-4,4,6,6-tetramethyl-1,5-dioxaspiro[2.4]heptan-7-one

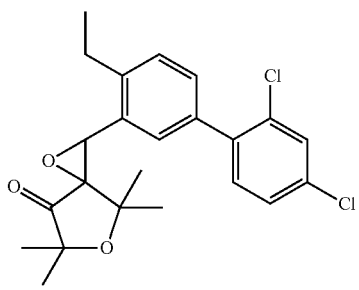 [SMILES: CCc1ccc(-c2ccc(Cl)cc2Cl)cc1C1OC12C(=O)C(C)(C)OC2(C)C]

To a solution of 4-[1-(2',4'-dichloro-4-ethylbiphenyl-3-yl)-methylidene]-2,2,5,5-tetramethyldihydrofuran-3-one (0.500 g, 1.24 mmol) in toluene (3.7 ml) is added aqueous sodium hyperchlorite solution (3.30 g, 6.20 mmol, 14% active chlorine) and tetrabutylammonium hydrogen sulfate (0.013 g, 0.04 mmol), and the biphasic mixture is then stirred at 50° C. for 4 hours. The reaction mixture is then diluted with additional toluene, the phases separated, and the organic phase washed again with distilled water (×2). The organic phase is dried over sodium sulfate then concentrated in vacuo to afford 2-(2',4'-dichloro-4-ethylbiphenyl-3-yl)-4,4,6,6-tetramethyl-1,5-dioxaspiro[2.4]heptan-7-one as a white solid.

Step 4A: Preparation of 4-(2',4'-Dichloro-4-ethylbiphenyl-3-yl)-2,2,6,6-tetramethylpyran-3,5-dione

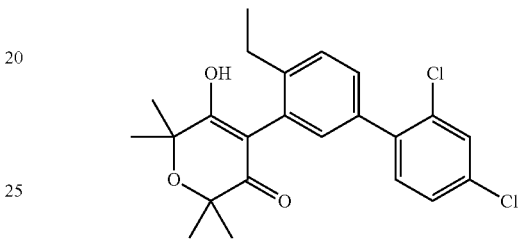

To an ice-cold solution of concentrated sulphuric acid (6 ml) is added a second solution of 2-(2',4'-dichloro-4-ethylbiphenyl-3-yl)-4,4,6,6-tetramethyl-1,5-dioxaspiro[2.4]heptan-7-one (1.90 g, 0.0045 mol) in 1,2-dichloroethane (6 ml) dropwise over 5 mins. This biphasic mixture is stirred vigorously for 2 hours at 0° C., then is poured into ice and extracted with diethyl ether. All organics are combined, washed with brine, dried over magnesium sulfate then concentrated in vacuo. The crude product is purified by flash column chromatography (5% ethyl acetate in isohexane to 25% ethyl acetate in isohexane) to afford 4-(2',4'-dichloro-4-ethylbiphenyl-3-yl)-2,2,6,6-tetramethylpyran-3,5-dione as a yellow gum.

1H NMR (CDCl$_3$): δ 7.48 (d, 1H), 7.43 (m, 2H), 7.30 (m, 2H), 7.13 (d, 1H), 5.71 (br. s, 1H), 2.55-2.44 (m, 2H), 1.62 (s, 6H), 1.49 (app. d, 6H), 1.17 (t, 3H).

Step 4B: Preparation of 4-(2',4'-Dichloro-4-ethylbiphenyl-3-yl)-2,2,6,6-tetramethylpyran-3,5-dione

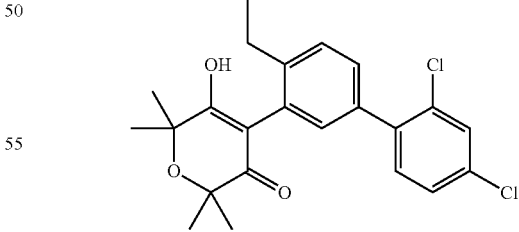

To a solution of 2-(2',4'-dichloro-4-ethylbiphenyl-3-yl)-4,4,6,6-tetramethyl-1,5-dioxaspiro[2.4]heptan-7-one (0.0418 g, 0.10 mmol) in toluene (0.3 ml) is added p-toluenesulfonic acid monohydrate (0.019 g, 0.10 mmol). The mixture is then heated at 150° C. for 1 hour, after which it is allowed to cool to room temperature. The reaction mixture is poured into distilled water, dried over sodium sulfate, then concentrated in vacuo to afford 4-(2',4'-dichloro-4-ethylbiphenyl-3-yl)-2,2,6,6-tetramethylpyran-3,5-dione.

Example P11

Preparation of 4-(5-Bromo-2-difluoromethoxyphenyl)-2,2,6,6-tetramethylpyran-3,5-dione

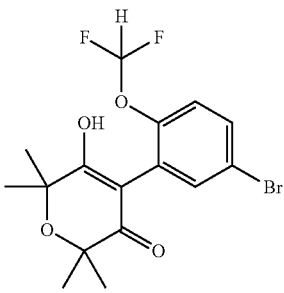

Step 1: Preparation of 5-Bromo-2-difluoromethoxybenzaldehyde

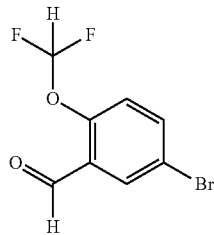 [SMILES: O=Cc1cc(Br)ccc1OC(F)F]

To a suspension of 5-bromosalicylaldehyde (7.60 g, 0.038 mol) and cesium carbonate (17.30 g, 0.053 mol) in anhydrous N,N-dimethylformamide (55 ml) is added sodium chlorodifluoroacetate (13.30 g, 0.087 mol) followed by distilled water (10 ml). The reaction mixture is heated at 100° C. for 6 hours (large pieces of solid are broken-up with a spatula), then allowed to cool to room temperature and is quenched with concentrated hydrochloric acid (15 ml). After stirring for a further 2 hours the reaction mixture is diluted with distilled water and extracted with ethyl acetate (×2). Organic fractions are combined, washed with 2M aqueous sodium hydroxide, brine, then dried over magnesium sulfate. The suspension is filtered and the filtrate concentrated in vacuo to afford 5-bromo-2-trifluoromethoxybenzaldehyde (5.66 g) of sufficient purity to use directly in the next step.

Step 2: Preparation of 4-[1-(5-Bromo-2-difluoromethoxyphenyl)methylidene]-2,2,5,5-tetramethyldihydrofuran-3-one

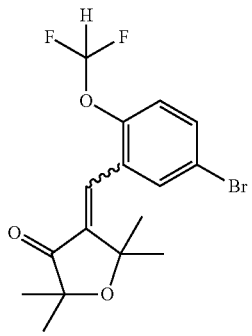 [SMILES: CC1(C)OC(C)(C)C(=Cc2cc(Br)ccc2OC(F)F)C1=O]

To an ice-cold solution of 2,2,5,5-tetramethyldihydrofuran-3-one (3.60 g, 0.025 mol) in anhydrous 1,2-dimethoxyethane (8 ml) is added sodium methoxide (1.51 g, 0.028 mol) in one portion. After stirring at this temperature for 5 minutes a solution of 5-bromo-2-difluoromethoxy-benzaldehyde (5.66 g, 0.023 mol) in 1,2-dimethoxyethane (8 ml) is added dropwise over 10 mins, followed by stirring at 0° C. for a further 1 hour. After warming to room temperature the reaction mixture is diluted with ether and washed with 2M hydrochloric acid (×2). Organic fractions are combined, dried over magnesium sulfate and evaporated in vacuo to afford 4-[1-(5-bromo-2-difluoromethoxyphenyl)methylidene]-2,2,5,5-tetramethyldihydrofuran-3-one (8.89 g) as an orange oil.

Step 3: Preparation of 2-(5-Bromo-2-difluoromethoxyphenyl)-4,4,6,6-tetramethyl-1,5-dioxaspiro[2.4]heptan-7-one

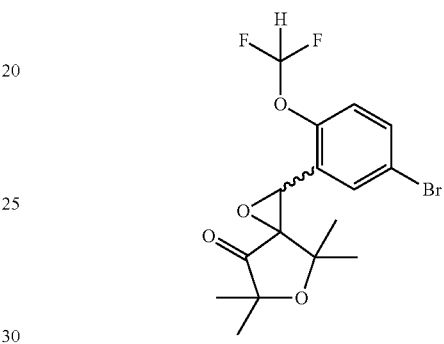

To a solution of 4-[1-(5-bromo-2-difluoromethoxyphenyl)methylidene]-2,2,5,5-tetramethyldihydrofuran-3-one (8.89 g, 0.023 mol) in methanol (380 ml) at 35° C. is added 50% aqueous hydrogen peroxide (2.30 ml, 0.034 mol), immediately followed by 2M aqueous lithium hydroxide (2.30 ml, 0.0046 mmol). After stirring at this temperature for 1 hour the reaction mixture is allowed to cool, then quenched with 10% sodium metabisulfite solution (negative KI-starch indicator test). The reaction mixture is extracted with diethyl ether (×3), then the organic phase is further washed with saturated aqueous sodium bicarbonate (×2) then brine. All organics are combined, dried over magnesium sulfate, filtered and the filtrate concentrated in vacuo to afford 2-(5-bromo-2-difluoromethoxyphenyl)-4,4,6,6-tetramethyl-1,5-dioxaspiro[2.4]heptan-7-one (7.22 g) a yellow gum.

Step 4: Preparation of 4-(5-Bromo-2-difluoromethoxyphenyl)-2,2,6,6-tetramethylpyran-3,5-dione

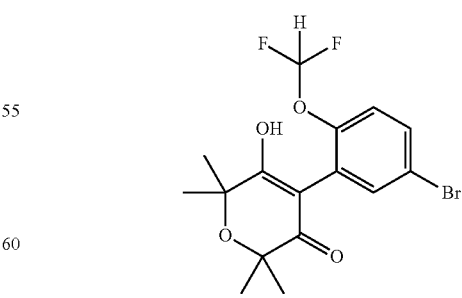

To an ice-cold solution of concentrated sulphuric acid (12 ml) is added a second solution of 2-(5-bromo-2-difluoromethoxyphenyl)-4,4,6,6-tetramethyl-1,5-dioxaspiro[2.4]heptan-7-one (7.22 g, 18.00 mmol) in 1,2-dichloroethane (12 ml) dropwise over 5 minutes. This biphasic mixture is stirred vigorously for 2 hours at 0° C., then allowed to stand at room temperature overnight. The reaction mixture is poured into ice-water, rinsing with a small amount of additional 1,2-dichloroethane/water, then concentrated under vacuum to remove all organic solvents. The crude product is next extracted into ethyl acetate (×3), than all organics are combined, washed with brine, and dried over magnesium sulfate. The suspension is filtered and the filtrate is concentrated in vacuo then purified by flash column chromatography (10% to 25% ethyl acetate in hexane as eluant) to give an oil which is triturated with hexanes to afford 4-(5-bromo-2-difluoromethoxyphenyl)-2,2,6,6-tetramethylpyran-3,5-dione (2.08 g) as a white solid.

1H NMR (CDCl$_3$): δ 7.54 (dd, 0.75H, isomer A), 7.51 (dd, 0.25H, isomer B), 7.37 (d, 0.75H, isomer A), 7.32 (d, 0.25H, isomer B), 7.15 (d, 0.75H, isomer A), 7.06 (d, 0.25H, isomer), 6.32 (t, 0.75H, isomer A), 6.29 (t, 0.25H, isomer B) 1H), 5.86 (s, 0.75H, isomer A), 5.28 (s, 0.25H, isomer A), 1.58-1.44 (m, 12H, isomers A and B).

What is claimed is:

1. A process for the preparation of a compound of formula (A)

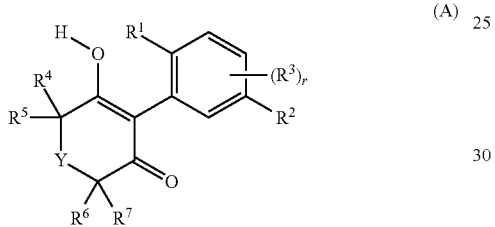

which comprises reacting a compound of formula (I)

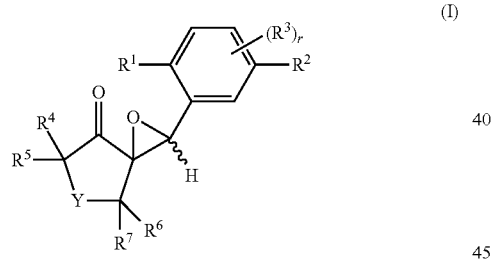

with an acid;
and wherein:
$R^1$ is halogen, $C_1$-$C_4$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkylsulfinyl, or $C_1$-$C_4$alkylsulfonyl;

$R^2$ is halogen, aryl or heteroaryl; or aryl or heteroaryl both substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, phenoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_3$-$C_6$cycloalkyl, $C_1$-$C_4$alkylsulfonyloxy, $C_1$-$C_4$haloalkylsulfonyloxy, $C_1$-$C_4$alkoxy$C_1$-$C_4$alkyl, $C_1$-$C_{14}$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, nitro, cyano, thiocyanato, hydroxy, amino, $C_1$-$C_6$alkylamino, $C_1$-$C_6$dialkylamino, $C_3$-$C_6$cycloalkylamino, morpholino, thiomorpholino, $C_1$-$C_6$alkylcarbonylamino, $C_1$-$C_6$alkoxycarbonylamino, $C_3$-$C_6$ alkenyloxycarbonylamino, $C_3$-$C_6$ alkynyloxycarbonylamino, $C_1$-$C_6$ alkylaminocarbonylamino, di($C_1$-$C_6$alkyl)aminocarbonylamino, formyl, $C_1$-$C_6$alkyl-carbonyl, $C_2$-$C_6$alkenylcarbonyl, $C_2$-$C_6$alkynylcarbonyl, carboxy, $C_1$-$C_6$alkoxycarbonyl, $C_3$-$C_6$alkenyloxycarbonyl, $C_3$-$C_6$alkynyloxycarbonyl, carboxamido, $C_1$-$C_6$alkylaminocarbonyl, di($C_1$-$C_6$alkyl)aminocarbonyl, $C_1$-$C_6$alkylcarbonyloxy, $C_1$-$C_6$alkylaminocarbonyloxy, di($C_1$-$C_6$alkyl)aminocarbonyloxy or $C_1$-$C_6$alkylthiocarbonylamino;

r is 0, 1, 2 or 3;

$R^3$, if r is 1, is $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, cyano or nitro; or the substituents $R^3$, if r is 2 or 3, independently of each other, are $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, cyano or nitro;

Y is O; and $R^4$, $R^5$, $R^6$ and $R^7$ independently of each other, are hydrogen, ethyl or methyl and wherein:
"aryl" means phenyl or naphthyl; and
"heteroaryl" means thienyl, furyl, pyrrolyl, isoxazolyl, oxazolyl, oxetanyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl or pyridazinyl, or, where appropriate, an N-oxide or a salt thereof.

2. A process according to claim 1, wherein $R^1$ is halogen, $C_1$-$C_4$alkyl, $C_1$-$C_4$haloalkyl, $C_3$-$C_6$cycloalkyl or $C_1$-$C_4$-haloalkoxy.

3. A process according to claim 1, wherein $R^2$ is halogen, aryl or heteroaryl; or aryl or heteroaryl both substituted by halogen, $C_1$-$C_4$alkyl, $C_1$-$C_4$haloalkyl, phenoxy, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

4. A process according to claim 1, wherein $R^2$ is phenyl, thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, pyridazinyl, oxadiazolyl or thiadiazolyl, or an N-oxide or a salt thereof, where these rings are unsubstituted or substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

5. A process according to claim 1, wherein $R^2$ is phenyl or pyridyl, or phenyl or pyridyl both substituted by halogen, nitro, cyano, $C_1$-$C_2$alkyl, $C_1$-$C_2$haloalkyl, $C_1$-$C_2$alkoxy or $C_1$-$C_2$haloalkoxy.

6. A process according to claim 1, wherein $R^2$ is phenyl substituted at the para-position by halogen and optionally further substituted by halogen, nitro, $C_1$-$C_2$alkyl, $C_1$-$C_2$haloalkyl, $C_1$-$C_2$alkoxy or $C_1$-$C_2$haloalkoxy.

7. A process according to claim 1, wherein $R^2$ is phenyl substituted at the para-position by chlorine and optionally further substituted by halogen, nitro, $C_1$-$C_2$alkyl, $C_1$-$C_2$haloalkyl, $C_1$-$C_2$alkoxy or $C_1$-$C_2$haloalkoxy.

8. A process according to claim 1, wherein either $R^3$ is hydrogen, which means that r is 0, or $R^3$ is $C_1$-$C_6$alkyl.

9. A process according to claim 1, wherein $R^3$ is hydrogen, which means that r is 0.

10. A process according to claim 1, wherein $R^4$, $R^5$, $R^6$ and $R^7$, independently of each other, are ethyl or methyl.

11. A process according to claim 1, wherein $R^1$ is ethyl, methyl or cyclopropyl;

$R^2$ is phenyl or phenyl substituted by halogen or $C_1$-$C_2$alkyl;

$R^3$ is hydrogen, which means that r is 0; and $R^4$, $R^5$, $R^6$ and $R^7$, independently of each other, are $C_1$-$C_2$alkyl.

12. A process according to claim 1, wherein the acid is a Brönsted acid or a Lewis acid.

13. A process according to claim 1, wherein the acid is a Brönsted acid which is a mineral acid or an organic acid.

14. A process according to claim 1, in which a suitable solvent which is chosen to be compatible with the acid is used.

15. A process according to claim 14, wherein the suitable solvent is a chlorinated hydrocarbon, an alcohol, an ether, an aromatic, or an organic acid, or a mixture of such solvents.

16. A process according to claim 15, wherein the suitable solvent is dichloromethane, dichloroethane, diethyl ether, acetic acid, formic acid, toluene, benzene, methanol, ethanol, isopropanol or tetrahydrofuran, or a mixture of such solvents.

17. A process according to claim 1, wherein the reaction temperature is within the range of between −50° C. and 83° C.

18. A process according to claim 1, wherein the reaction temperature is within the range of between −50° C. and 40° C.

19. The process of claim 1, wherein the compound of formula (I) is prepared by reacting a compound of formula (F)

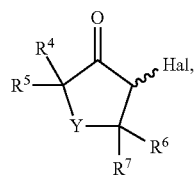

(F)

wherein Y, $R^4$, $R^5$, $R^6$, and $R^7$ are as defined in claim 1, Hal is chlorine, bromine or iodine, with a compound of formula (D)

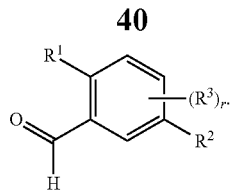

(D)

wherein $R^1$, $R^2$, $R^3$ and r are as defined in claim 1.

20. The process of claim 1, wherein the compound of formula (I) is prepared by reacting a compound of formula (C)

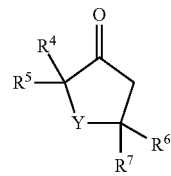

(C)

wherein Y, $R^4$, $R^5$, $R^6$, and $R^7$ are as defined in claim 1, with a compound of formula (D)

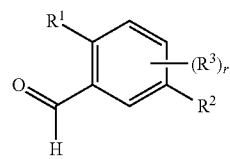

(D)

wherein $R^1$, $R^2$, $R^3$ and r are as defined in claim 1, to give a compound of formula (B)

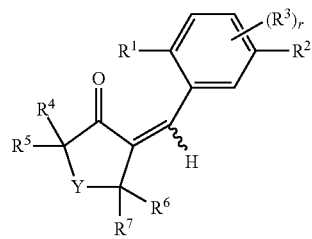

and further reaction with an oxidizing agent.

* * * * *